US010278966B2

(12) United States Patent
Jiang et al.

(10) Patent No.: US 10,278,966 B2
(45) Date of Patent: May 7, 2019

(54) METHOD OF ISOLATING QUATERNARY PHENANTHROINDOLIZIDINE ALKALOIDS WITH G-QUADUPLEX DNA BINDING ACTIVITY FROM *TYLOPHRA ATROFOLLICULATA*, COMPOSITIONS COMPRISING THEM AND THEIR MEDICAL USE

(71) Applicant: Macau University of Science and Technology, Taipa (MO)

(72) Inventors: Zhi-Hong Jiang, Taipa (MO); Jing-Rong Wang, Taipa (MO); Cheng-Yu Chen, Taipa (MO); Guo-Yuan Zhu, Taipa (MO)

(73) Assignee: Macau University of Science and Technology, Taipa (MO)

( * ) Notice: Subject to any disclaimer, the term of this patent is extended or adjusted under 35 U.S.C. 154(b) by 0 days.

(21) Appl. No.: 15/142,407

(22) Filed: Apr. 29, 2016

(65) Prior Publication Data
US 2017/0312267 A1 Nov. 2, 2017

(51) Int. Cl.
*A61K 31/4745* (2006.01)
*A61K 36/27* (2006.01)
(52) U.S. Cl.
CPC .......... *A61K 31/4745* (2013.01); *A61K 36/27* (2013.01)
(58) Field of Classification Search
CPC .............................. A61K 31/4745; A61K 36/24
See application file for complete search history.

(56) References Cited

U.S. PATENT DOCUMENTS 7,652,027 B2 * 1/2010 Lee ...................... C07D 471/04
514/280

OTHER PUBLICATIONS

Dhiman et al (Chemical Papers, 2013, 67(2), 245-248).*
Kyo et al, Oncogene, 2002, 21, 688-697. (Year: 2002).*
Soares, 2010, A dissertation submitted to the faculty of the University of North Carolina at Chapel Hill. (Year: 2010).*
Bhadra et al, Biochimca et Biophysica Acta, 2011, 1810, 485-496 (Year: 2011).*
L. R Kelland, "Overcoming the immortality of tumour cells by telomere and telomerase based cancer therapeutics—current status and future prospects", European Journal of Cancer, vol. 41, pp. 971-979, 2005.
H. J. Lipps, and D. Rhodes, "G-quadruplex structures: in vivo evidence and function", Trends in Cell Biology, vol. 19, No. 8, pp. 414-422, 2009.
A. J. Zaug, E. R. Podell and T. R. Cech, "Human POT1 disrupts telomeric G-quadruplexes allowing telomerase extension in vitro", PANS, vol. 102, No. 31, pp. 10864-10869, 2005.
V. Gabelica, E. S. Baker, M. P. Teulade-Fichou, E. D. Pauw and M. T. Bowers, "Stabilization and Structure of Telomeric and c-myc Region Intramolecular G-Quadruplexes: The Role of Central Cations and Small Planar Ligands" J. Am. Chem. Soc., vol. 129, No. 4, pp. 895-904, 2007.
D. Sun, B. Thompson, B. E. Cathers, M. Salazar, S. M. Kerwin, J. O. Trent, T. C. Jenkins, S. Neidle and L. H. Hurley, "Inhibition of Human Telomerase by a G-Quadruplex-Interactive Compound", J. Med. Chem., vol. 40, No. 14, pp. 2113-2116, 1997.
T. M. Ou, Y. j. Lu, J. H. Tan, Z. S. Huang, K. Y. Wong and L. Q. Gu, "G-Quadruplexes: Targets in Anticancer Drug Design", ChemMedChem, vol. 3, pp. 690-713, 2008.
J. L. Beck, M. L. Colgrave, S. F. Ralph and M. M. Sheil, "Electrospray ionization mass spectrometry of oligonucleotide complexes with drugs, metals, and proteins", Mass Spectrometry Reviews, vol. 20, pp. 61-87, 2001.
X. Huang, S. Gao, L. Fan, S. Yu and X. Liang, "Cytotoxic Alkaloids from the Roots of Tylophora atrofolliculata", Planta Med, vol. 70, pp. 441-445, 2004.
A. G. Damu, P. C. Kuo, L. S. Shi, C. Y. Li, C. S. Kuoh, P. L. Wu and T. S. Wu, "Phenanthroindolizidine Alkaloids from the Stems of Ficus septica", J. Nat. Prod., vol. 68, No. 7, pp. 1071-1075, 2005.
A. G. Damu, P. C. Kuo, L. S. Shi, C. Y. Li, C. R. Su and T. S. Wu, "Cytotoxic Phenanthroindolizidine Alkaloids from the Roots of Ficus septica", Planta Med., vol. 75, pp. 1152-1156, 2009.
D. Staek, A. K. Lykkeberg, J. Christensen, B. A. Budnik, F. Abe and J. W. Jaroszewski, "In Vitro Cytotoxic Activity of Phenanthroindolizidine Alkaloids from Cynanchum vincetoxicum and Tylophora tanakae against Drug-Sensitive and Multidrug-Resistant Cancer Cells" J. Nat. Prod., vol. 65, No. 9, pp. 1299-1302, 2002.
Z. Xi, R. Zhang, Z. Yu, D. Ouyang and R. Huang, "Selective interaction between tylophorine B and bulged DNA", Bioorganic & Medicinal Chemistry Letters, vol. 15, pp. 2673-2677, 2005.
F. Abe, Y. Iwase, T. Yamauchi, K. Honda and N. Hayashi, "Phenanthroindolizidine alkaloids from Tylophora tanakae", Phytochemistry, vol. 39, No. 3, pp. 695-699, 1995.
M. Ali, S. H. Ansari and J. S. Qadry, "Rare Phenanthroindolizidine Alkaloids and a Substituted Phenanthrene, Tyloindane, from Tylophora Indica", Journal of Natural Products, vol. 54, No. 5, pp. 1271-1278, 1991.
M. Ali and K. K. Bhutani, "Minor alkaloids of Tylophora Hirsute", Phytochemistry, vol. 26, No. 7, pp. 2089-2092, 1987.

(Continued)

*Primary Examiner* — Sudhakar Katakam
(74) *Attorney, Agent, or Firm* — Renner Kenner Greive Bobak Taylor

(57) ABSTRACT

A method of isolating at least one phenanthroindolizidine alkaloid, in particular with telomerase inhibitory activity, from *Tylophora atrofolliculata* is used to isolate and obtain for example about six to eight phenanthroindolizidine alkaloids, including at least four new phenanthroindolizidine alkaloids which have not been previously isolated. Experimental tests confirmed an exceptional telomerase inhibitory activity of the phenanthroindolizidine alkaloids isolated. A pharmaceutical composition includes at least one phenanthroindolizidine alkaloid and at least one pharmaceutical tolerable excipient. Still further, a method of treating a subject suffering from cancer includes administering at least one phenanthroindolizidine alkaloid isolated from *Tylophora atrofolliculata*. Also, a method of treating a subject suffering from cancer includes administering to the subject at least one phenanthroindolizidine alkaloid having certain formula.

7 Claims, 7 Drawing Sheets

(56) References Cited

OTHER PUBLICATIONS

M. Ali and K. K. Bhutani, "Alkaloids from Tylophora Indica", Phytochemistry, vol. 28, No. 12, pp. 3513-3517, 1989.
K. K. Bhutani, M. Ali and C. K. Atal, "Alkaloids from Tylophora Hirsute", Phytochemistry, vol. 23, No. 8, pp. 1765-1769, 1984.
K. K. Bhutani, M. Ali and C. K. Atal, "13a-hydroxytylophorine from Tylophora Hirsute", Phytochemistry, vol. 24, No. 11, pp. 2778-2780, 1985.
H. K. Desai, D. H. Gawad, T. R. Govindachari, B.S. Joshi, V. N. Kamat, J. D. Modi, P. C. Parthasarathy, J. Radhakrishnan, M. N. Shanbhag, A. R. Sidhaye and N. Viswanathan, "Chemical Investigation of Indian Plants: Part VII", Indian Journal of Chemistry, vol. 11, No. 8, pp. 840-842, 1973.
H. Lv, J. Ren, S. Ma, S. Xu, J. Qu, Z. Liu, Q. Zhou, X. Chen, and S. Yu, "Synthesis, Biological Evaluation and Mechanism Studies of Deoxytylophorinine and Its Derivatives as Potential Anticancer Agents", PLoS One, vol. 7, No. 1, e30342, pp. 1-16, 2012.
T. H. Chuang, S. J. Lee, C. W. Yang and P. L. Wu, "Expedient synthesis and structure-activity relationships of phenanthroindolizidine and phenanthroquinolizidine alkaloids", Organic & Biomolecular Chemistry, vol. 4, pp. 860-867, 2006.
L.P. Bai, Z. Cai, Z Z. Zhao, K. Nakatani and Z. H. Jiang, "Site-specific binding of chelerythrine and sanguinarine to single pyrimidine bulges in hairpin DNA", Anal. Bioanal Chemistry, vol. 392, pp. 709-716, 2008.
L. P. Bai, Z Z. Zhao, Z. Cai and Z. H. Jiang, "DNA-binding affinities and sequence selectivity of quaternary benzophenanthridine alkaloids sanguinarine, chelerythrine, and nitidine", Bioorganice & Medicinal Chemistry, vol. 14, pp. 5439-5445, 2006.
L. P. Bai, H. M. Ho, D. L. Ma, H. Yang, W. C. Fu and Z. H. Jiang, "Aminoglycosylation Can Enhance the G-Quadruplex Binding Activity of Epigallocatechin", PloS One, vol. 8, No. 1, e53962, pp. 1-10, 2013.
Y. Qin, J. Y. Pang, W. H. Chen, Z. Cai and Z. H. Jiang, "Synthesis, DNA binding affinities, and binding mode of berberine dimers", Bioorganice & Medicinal Chemistry, vol. 14, pp. 25-32, 2006.
L. P. Bai, M. Hagihara, K. Nakatani and Z. H. Jiang, "Recognition of Chelerythrine to Human Telomeric DNA and RNA G-quadruplexes", Scientific Report, vol. 4, No. 6767, pp. 1-10, 2014.

* cited by examiner

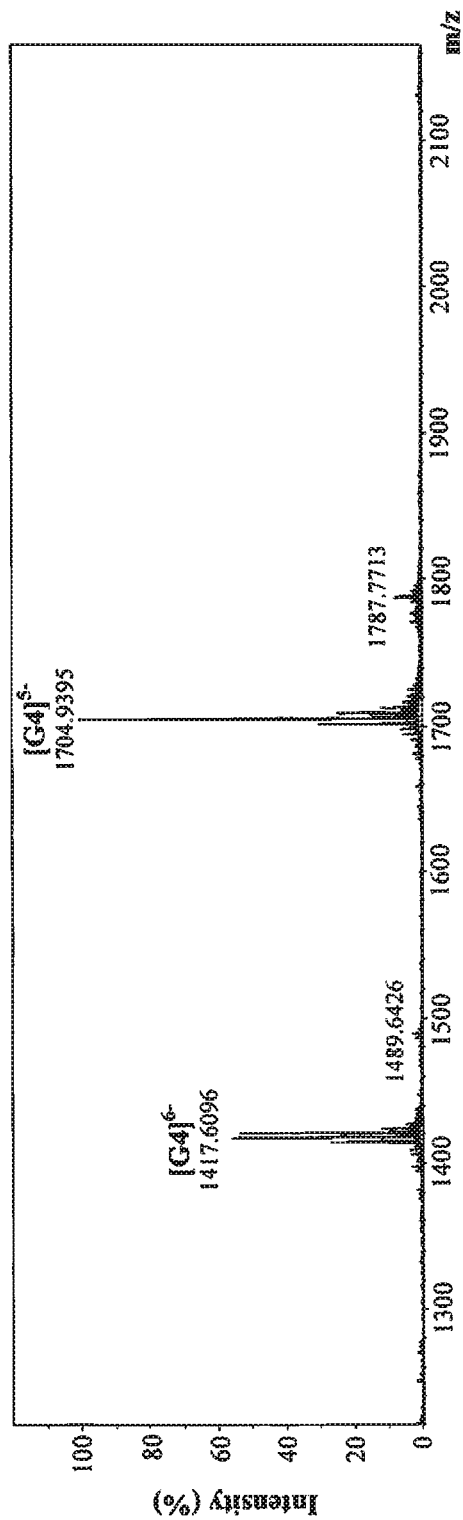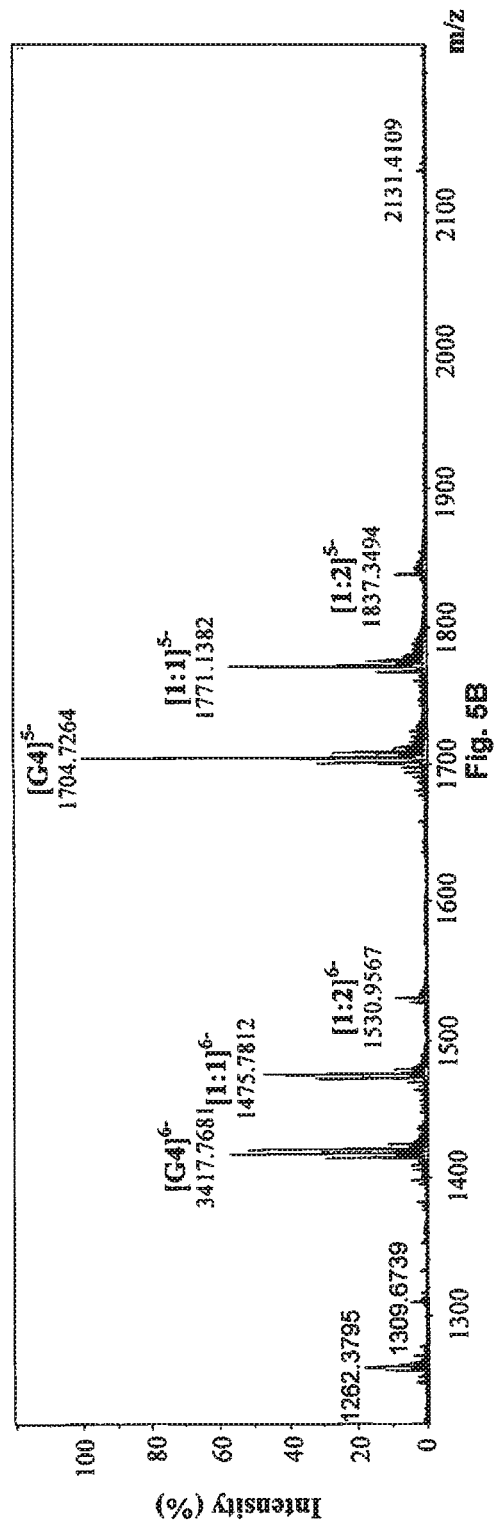
Fig. 5A
Fig. 5B

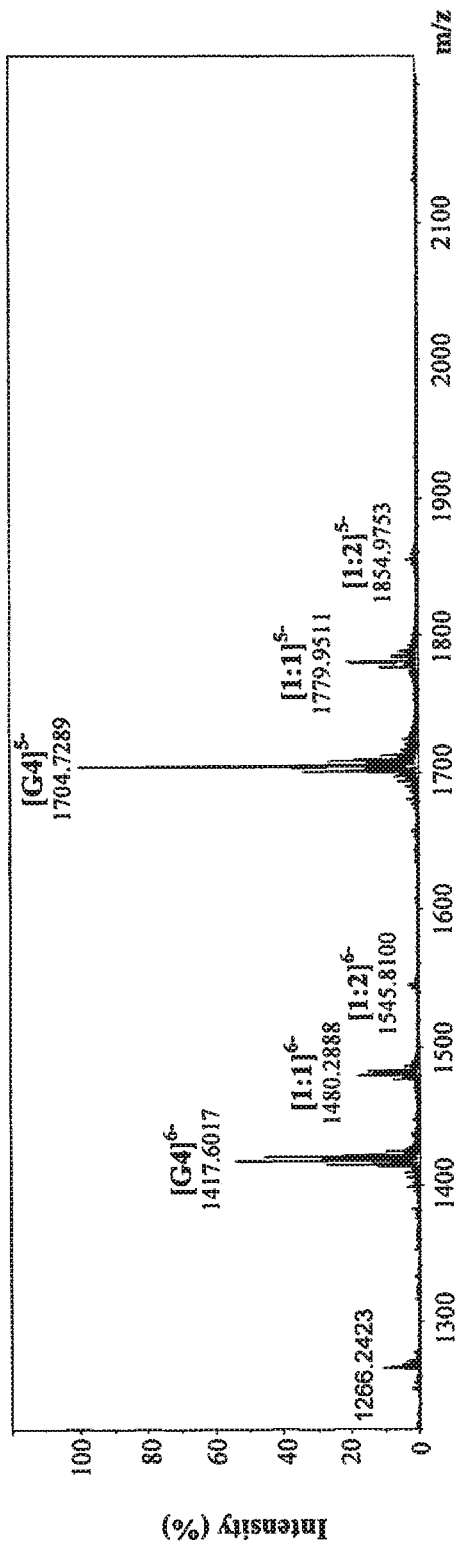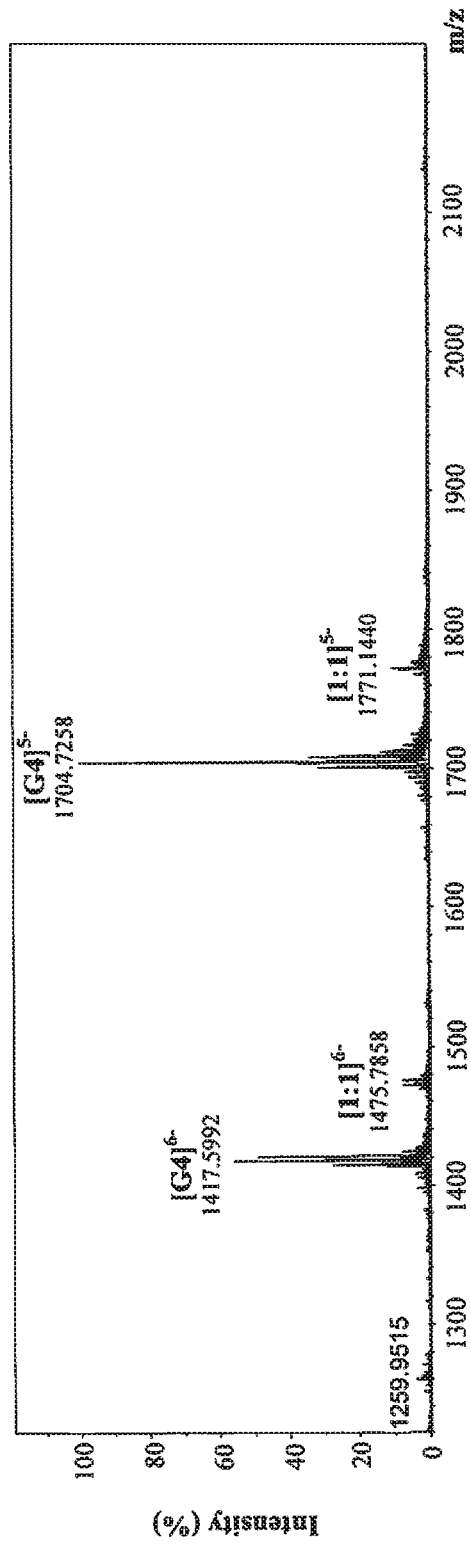

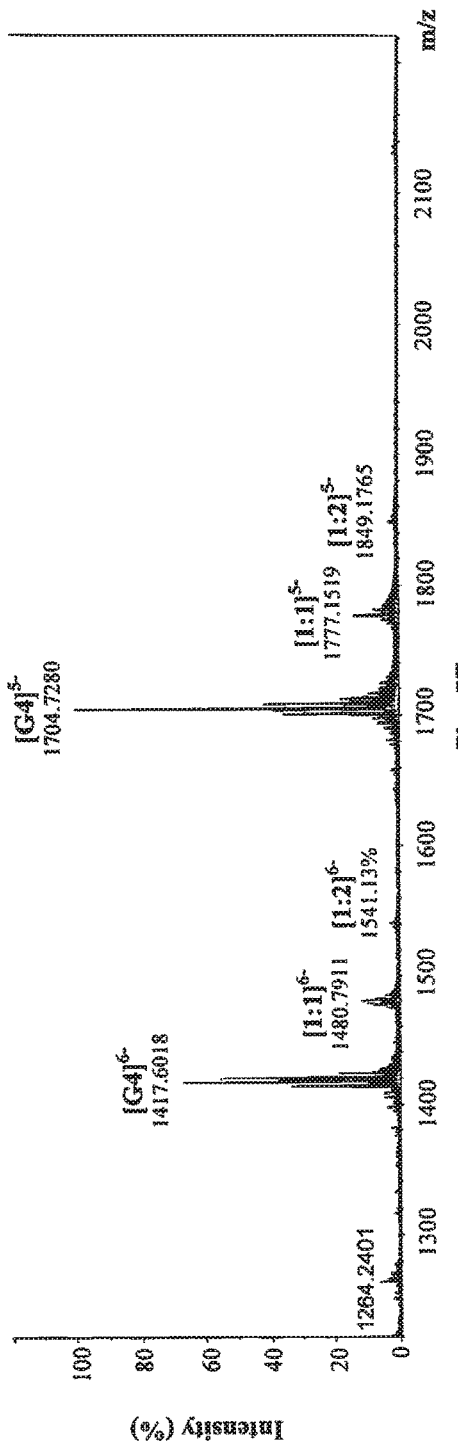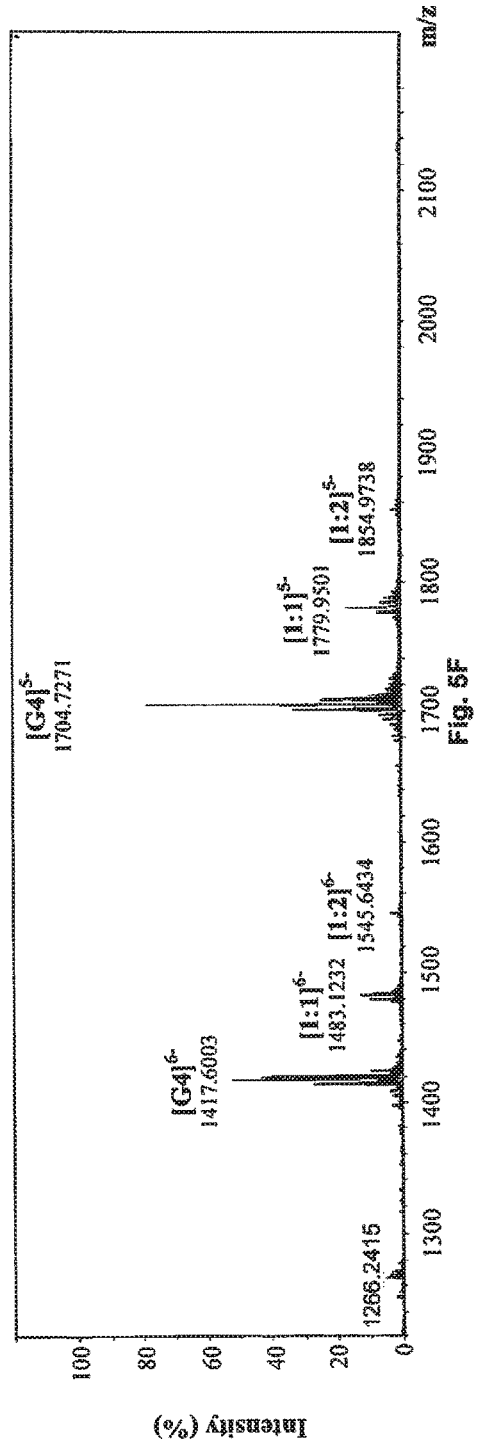

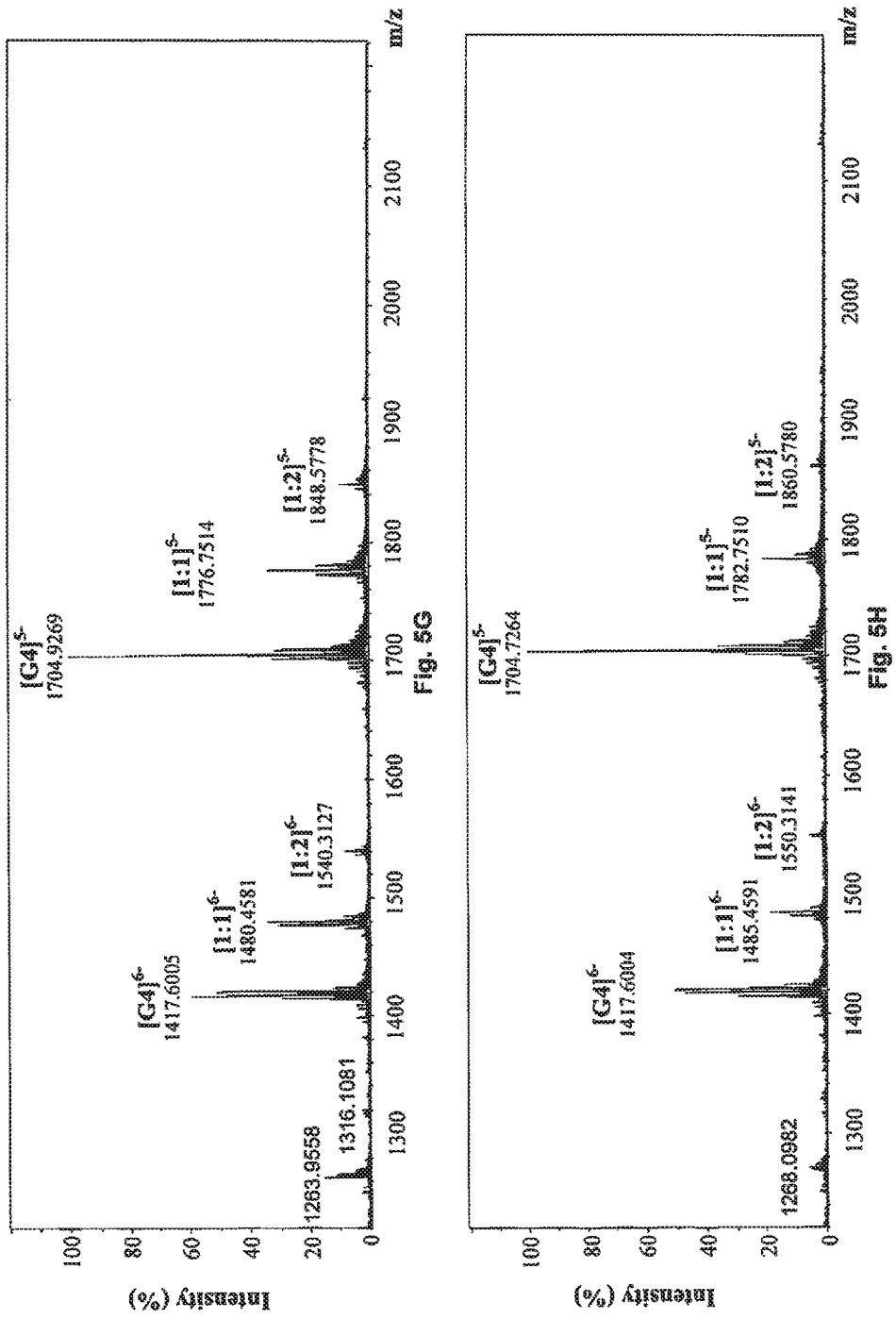

METHOD OF ISOLATING QUATERNARY PHENANTHROINDOLIZIDINE ALKALOIDS WITH G-QUADUPLEX DNA BINDING ACTIVITY FROM *TYLOPHRA ATROFOLLICULATA*, COMPOSITIONS COMPRISING THEM AND THEIR MEDICAL USE

TECHNICAL FIELD

The present invention relates to a method of isolating at least one phenanthroindolizidine alkaloid, in particular with telomerase inhibitory activity, from *Tylophora atrofolliculata*. The present invention also refers to a composition, in particular a pharmaceutical composition, comprising said the phenanthroindolizidine alkaloid and at least one excipient. Further, the present invention refers to a method of treating a subject suffering from cancer by administering a phenanthroindolizidine alkaloid isolated from *Tylophora atrofolliculata*.

BACKGROUND OF THE INVENTION

Telomeres generally refer to specific DNA-protein structures located at each end of a chromosome, which protect the end of the chromosome from unnecessary deterioration, repair and inter-chromosomal fusion. In normal cellular process, cells divide and lose a portion of the telomeres in each cell division. The length of a telomere is reduced each time, i.e. telomere shortening. When a telomere length reaches a limit, i.e. becomes too short to exhibit the protective effect of a telomere, the cell undergoes programmed cell death and eventually dies.

Telomerase, also known as telomere terminal transferase, is a reverse transcriptase enzyme that synthesizes telomeric DNA sequences and adds the DNA sequences to the 3' end of telomeres. It keeps the telomere from wearing down too much by maintaining the length of the telomere. I.e. telomerase counteracts with telomere shortening. Notably, it has been found that telomerase is highly activated, i.e. overly expressed, in most cancers and immortalized cells. Telomerase facilitates the elongation of the telomeres and keeps cancer cells immortal. Accordingly it is believed that inhibiting the activity of the telomerase and reactivating telomere shortening help to trigger programmed cell death of the cancer cells and is a suitable approach for treating cancer.

Telomeric G-quadruplexes which are formed spontaneously by telomeric DNA folding may hinder the recruitment of telomerase. Studies have confirmed that a stabilization of telomeric G-quadruplexes via non-covalent interaction with small organic molecules is a suitable way to inhibit telomerase activity. For characterizing the interaction between small organic molecules and telomeric G-quadruplexes, electrospray ionization time-of-flight mass spectrometry (ESI-TOF-MS) is usually applied owing to its sensitivity and reliability to determine stoichiometries, relative binding affinities (RBA) and equilibrium association constants of drug-DNA complexes.

As there remains a strong need for therapeutically effective compounds and improved ways for successfully treating cancer and in view of the highly promising approach of an inhibition of telomerase activity, having new compounds with sufficient telomerase activity is highly desirable. As usual, it would generally be desirable to have compounds with reduced risk for side effects, which can be prepared in a cost-effective way and are directed only at tumor cells.

Recently, Traditional Chinese medicine as well as complementary and alternative medicine has getting popular providing a lot of treatment options. Traditional Chinese medicines based on plant materials as well as plants or respective components gained from plants usually allow for treatment of various diseases and conditions while bearing a reduced risk for side effects. In view of the rich medicinal plant resources, available respective medicines can usually be produced in a cost-effective way. Accordingly, there has been a lot of research with regard to plants and respective ingredients for treatment of several diseases and conditions.

For example, *Tylophora atrofolliculata* (Asclepiadaceae) is already used as a traditional medicine. The roots of *Tylophora atrofolliculata* which are mainly distributed in the Guangxi Province in the Southwest of China have been used such as for the treatment of rheumatism. Components isolated from said plant include phenanthroindolizidine alkaloids (Huang, X. et al., Planta Med., 2004, 70, 441-445, Abe, F. et al., Chem. Pharm. Bull, 1998, 46, 767-769, Abe, F. et al., Phytochemistry, 1995, 39, 695-699, Ali, M. et al., J. Nat. Prod., 1991, 54, 1271-1278, M. Ali and K. K. Bhutani, Phytochemistry, 1987, 26, 2089-2092, Ali, M. and Bhutani, K. K., Phytochemistry, 1989, 28, 3513-3517, Bhutani, K. K. et al., Phytochemistry, 1985, 24, 2778-2780, Dhiman, M. et al., Chem. Pap.-Chem. Zvesti, 2013, 67, 245-248), however, only alkaloids such as tylophoridicine C-F, tylophorinine, tylophorinidine have been isolated from this plant so far. Members of the phenanthroindolizidine alkaloid class are generally well known to possess multiple pharmacological effects, such as anti-inflammatory, antifungal, antibacterial, and antiviral activities. Besides, pronounced cytotoxicity of some phenanthroindolizidine alkaloids against various cancer cell lines attracted much attention in the discovery of anticancer drugs (Lee, Y. Z. et al., Planta Med., 2011, 77, 1932-1938, Cai, X. F. et al., J. Nat. Prod., 2006, 69, 1095-1097, Damu, A. G. et al., Planta Med., 2009, 75, 1152-1156, Damu, A. G. et al., J. Nat. Prod., 2005, 68, 1071-1075, Lykkeberg, A. K. et al., J. Nat. Prod., 2002, 65, 1299-1302).

In view of the presence of various different compounds in plants usually with completely different mode of action and therapeutic efficiency, there is a strong need for identifying and providing components in isolated form with suitable therapeutic efficiency such as with sufficient telomerase inhibitory activity for treatment of cancer. Having those active ingredients in isolated form could further reduce the risk of side effects or interactions resulting from the presence of further compounds limiting the therapeutic use.

SUMMARY OF THE INVENTION

The invention provides in a first aspect a method of isolating at least one phenanthroindolizidine alkaloid from *Tylophora atrofolliculata*, the method comprising steps of:
(i) subjecting *Tylophora atrofolliculata* plant material to a solvent extraction with an extraction solvent for obtaining a crude extract, wherein the extraction solvent comprises an aliphatic alcohol;
(ii) contacting the crude extract with a first and a second separation solvent for obtaining a first and a second layer, wherein the first separation solvent comprises water and the second separation solvent comprises an ester;
(iii) contacting the first layer with a third separation solvent comprising a halogenated hydrocarbon for forming a third layer;

(iv) contacting the first layer after step (iii) with a fourth separation solvent comprising an aliphatic alcohol for forming a fourth layer;
(v) subjecting the fourth layer to at least a first chromatographic separation step.

Preferably, the phenanthroindolizidine alkaloid is of Formula (1),

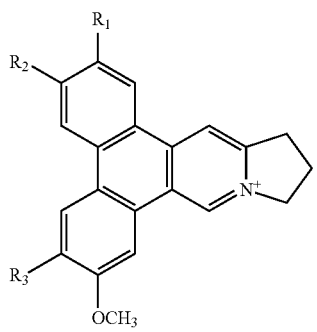

Formula (1)

wherein $R_1$, $R_2$ and $R_3$ are each independently selected from a hydrogen atom, a hydroxyl group, an alkyl group, or an alkoxy group, in particular $R_1$ is selected from H, OH or $OCH_3$ and $R_2$ and $R_3$ are each independently selected from OH or $OCH_3$.

The phenanthroindolizidine alkaloid isolated is in particular selected from the group consisting of:

a compound of Formula (2)

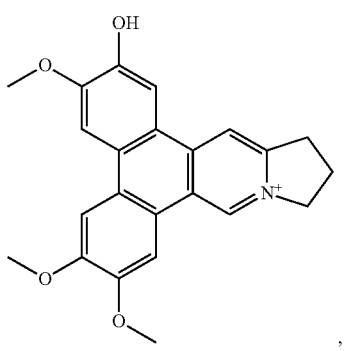

Formula (2)

a compound of Formula (3)

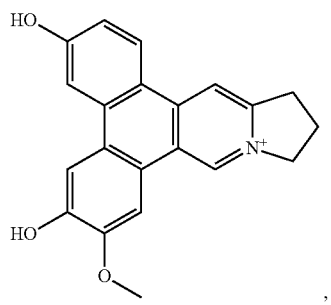

Formula (3)

a compound of Formula (4)

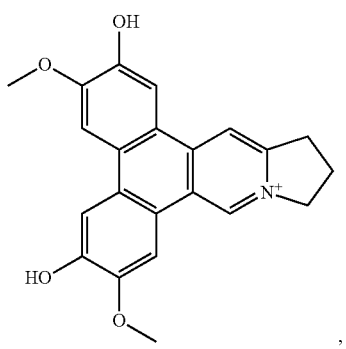

Formula (4)

and a compound of Formula (5)

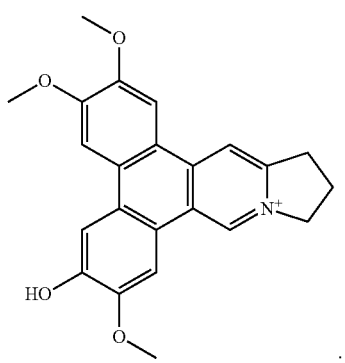

Formula (5)

The present invention further refers to a method of treating a subject suffering from cancer comprising administering an effective amount of at least one phenanthroindolizidine alkaloid isolated from *Tylophora atrofolliculata* with the method described before to the subject.

Preferably, the phenanthroindolizidine alkaloid is of Formula (1),

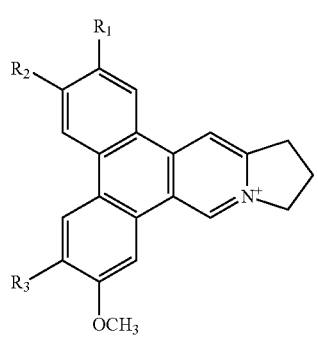

Formula (1)

wherein $R_1$, $R_2$ and $R_3$ are each independently selected from a hydrogen atom, a hydroxyl group, an alkyl group, or an alkoxy group, in particular $R_1$ is selected from H, OH or $OCH_3$ and $R_2$ and $R_3$ are each independently selected from OH or $OCH_3$.

Still further, the present invention refers to a composition, preferably a pharmaceutical composition, comprising and in particular essentially consisting of:
- at least one phenanthroindolizidine alkaloid, in particular as a pharmaceutically effective ingredient, isolated from *Tylophora atrofolliculata* according to the method described above, and
- a pharmaceutically tolerable excipient such as one or more of a diluent, a filler, a binder, a disintegrant, a lubricant, a coloring agent, a surfactant and a preservative.

Another aspect of the present invention relates to a method of treating a subject suffering from cancer comprising steps of:
- isolating at least one phenanthroindolizidine alkaloid from *Tylophora atrofolliculata* by the method described above, in particular a phenanthroindolizidine alkaloid of Formula (1),

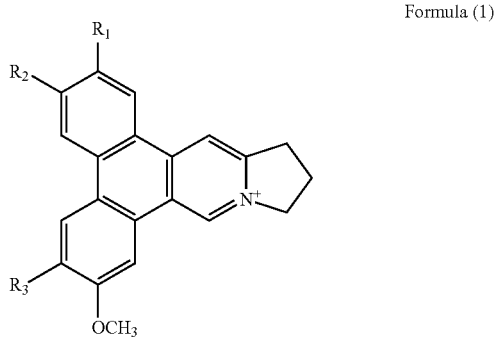

Formula (1)

wherein $R_1$, $R_2$ and $R_3$ are each independently selected from a hydrogen atom, a hydroxyl group, an alkyl group, or an alkoxy group, in particular $R_1$ is selected from H, OH or $OCH_3$ and $R_2$ and $R_3$ are each independently selected from OH or $OCH_3$;
- formulating the phenanthroindolizidine alkaloid into a pharmaceutical composition; and
- administering the pharmaceutical composition to a subject suffering from a cancer. The subject is preferably a human.

The method of the present invention of isolating at least one phenanthroindolizidine alkaloid from *Tylophora atrofolliculata* can be used to isolate and obtain for example about 7 phenanthroindolizidine alkaloids.

Among them 4 are new phenanthroindolizidine alkaloids, i.e. compounds having formula (2) to (5), which have not been previously isolated.

The phenanthroindolizidine alkaloids isolated from *Tylophora atrofolliculata* with the method of the present invention exhibit potent inhibitory effects on telomerase activity as they are able to effectively bind to the telomeric G-quadruplexes for inhibiting the telomerase activity. More specifically, when the phenanthroindolizidine alkaloids bind to the telomeric G-quadruplexes, the activity of telomerase which synthesizes telomeric DNA sequence at the 3' end of the telomere is significantly hindered. Telomere shortening occurs and triggers programmed cell death of the cancer cells.

Other features and aspects of the invention will become apparent by consideration of the following detailed description and accompanying drawings.

BRIEF DESCRIPTION OF THE DRAWINGS

FIG. 5A shows the negative ESI-TOF-MS spectrum of human telomeric sequence (G4).

FIG. 5B shows the negative ESI-TOF-MS spectrum of human telomeric sequence (G4) in the presence of an equimolar amount of sanguinarine which serves as a positive control.

FIG. 5C shows the negative ESI-TOF-MS spectrum of human telomeric sequence (G4) in the presence of an equimolar amount of compound of Formula (2), also referenced as compound 1.

FIG. 5D shows the negative ESI-TOF-MS spectrum of human telomeric sequence (G4) in the presence of an equimolar amount of compound of Formula (3), also referenced as compound 2.

FIG. 5E shows the negative ESI-TOF-MS spectrum of human telomeric sequence (G4) in the presence of an equimolar amount of compound of Formula (4), also referenced as compound 3.

FIG. 5F shows the negative ESI-TOF-MS spectrum of human telomeric sequence (G4) in the presence of an equimolar amount of compound of Formula (5), also referenced as compound 4.

FIG. 5G shows the negative ESI-TOF-MS spectrum of human telomeric sequence (G4) in the presence of an equimolar amount of compound of Formula (6), also referenced as compound 5.

FIG. 5H shows the negative ESI-TOF-MS spectrum of human telomeric sequence (G4) in the presence of an equimolar amount of compound of Formula (7), also referenced as compound 6.

DETAILED DESCRIPTION

Figure 1:
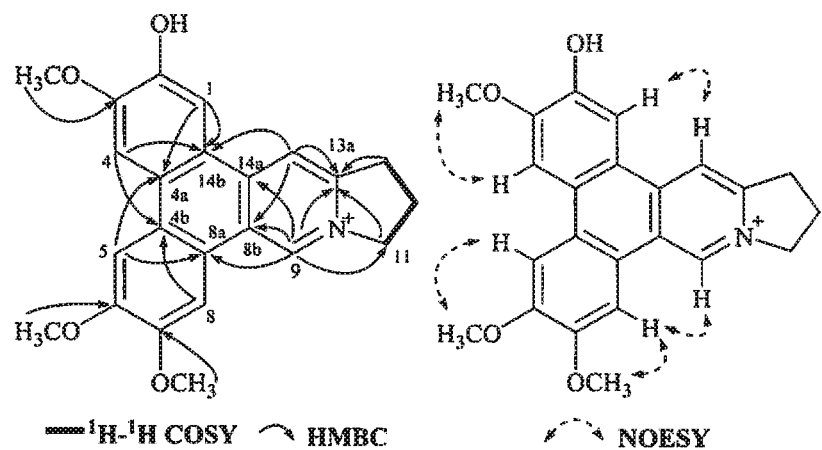
FIG. 1 shows the correlations observed in $^1$H-$^1$H COSY, HMBC, and NOESY spectra of compound of Formula (2), also referenced as compound 1.

The following preparations and examples are given to enable those skilled in the art to more clearly understand and to practice the present invention. They should not be considered as limiting the scope of the invention, but merely as being illustrative and for representing preferred embodiments thereof. The technical terms used in the present patent application have the meaning as commonly understood by a respective skilled person unless specifically defined otherwise.

As used herein and in the claims, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element.

In a first aspect, the invention provides a method of isolating at least one phenanthroindolizidine alkaloid from *Tylophora atrofolliculata*. The method of the present invention comprises steps of:

(i) subjecting *Tylophora atrofolliculata* plant material to a solvent extraction with an extraction solvent for obtaining a crude extract, wherein the extraction solvent comprises an aliphatic alcohol;

(ii) contacting the crude extract with a first and a second separation solvent for obtaining a first and a second layer, wherein the first separation solvent comprises water and the second separation solvent comprises an ester;

(iii) contacting the first layer with a third separation solvent comprising a halogenated hydrocarbon for forming a third layer;

(iv) contacting the first layer after step (iii) with a fourth separation solvent comprising an aliphatic alcohol for forming a fourth layer;

(v) subjecting the fourth layer to at least a first chromatographic separation step.

Optionally, the method includes further steps after step (v) of purifying the phenanthroindolizidine alkaloid.

The term "isolating" or "isolation" used herein means separating a combination of two or more or one single phenanthroindolizidine alkaloid from components present in the *Tylophora atrofolliculata* plant material. In particular, the method is for isolating a combination of at most 8, further preferred at most 7, still further preferred at most 6, further preferred at most two and in particular one single phenanthroindolizidine alkaloid, in particular an phenanthroindolizidine alkaloid with telomerase inhibitory activity, from *Tylophora atrofolliculata* plant material.

The term "purifying" as used herein refers to methods generally known to the skilled person for purifying compounds like evaporation, lyophilization or (re-)crystallization for obtaining a desired degree of purity, i.e. a desired degree of absence of impurities.

The at least one ingredient isolated from *Tylophora atrofolliculata* plant material is a phenanthroindolizidine alkaloid. "Alkaloids" are known to the skilled person as a class of components present in various plants characterized by a chemical structure with at least one nitrogen atom, usually at least one heterocyclic nitrogen atom. Alkaloids can be divided into several subgroups depending on the specific nitrogen containing heterocyclic ring system. Phenanthroindolizidine alkaloids represent a small subgroup of alkaloids and the term generally refers to compounds having a phenanthrene ring system fused with that of an indolizidine.

Preferably, the at least one phenanthroindolizidine alkaloid is of Formula (1),

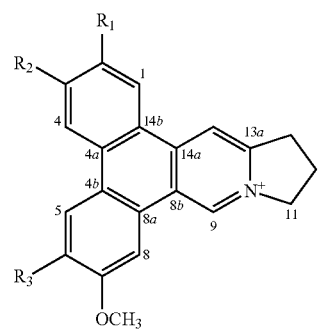

Formula (1)

wherein $R_1$, $R_2$ and $R_3$ are each independently selected from a hydrogen atom, a hydroxyl group, an alkyl group, or an alkoxy group, in particular $R_1$ is selected from H, OH or $OCH_3$ and $R_2$ and $R_3$ are each independently selected from OH or $OCH_3$.

The alkyl group is preferably a $C_1$-$C_4$ primary alkyl, preferably selected from a methyl group, an ethyl group, a propyl group or a butyl group, more preferably is a methyl group or an ethyl group. The alkoxy group is an alkyl group singularly bonded to an oxygen atom, i.e. having the formula of RO. Preferably, the alkoxy group is $C_1$-$C_4$ alkoxy group selected from a methoxy group, an ethoxy group, a n-propyloxy group, a sec-butyloxy group or an iso-butyloxy group. More preferably, the alkoxy group is a methoxy group or an ethyoxy group and in particular a methoxy group having the formula of $OCH_3$.

More preferably, the phenanthroindolizidine alkaloid is selected from the group consisting of:

a compound of Formula (2), also referenced as compound 1,

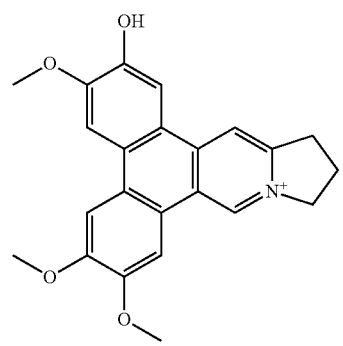

Formula (2)

a compound of Formula (3), also referenced as compound 2,

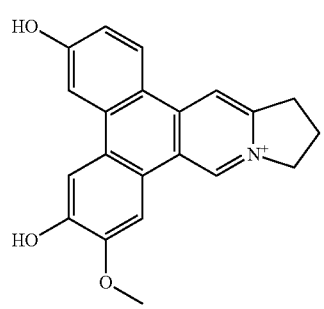

Formula (3)

a compound of Formula (4), also referenced as compound 3,

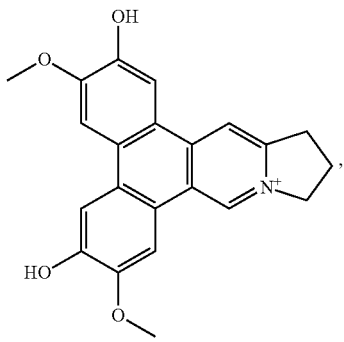

Formula (4)

a compound of Formula (5), also referenced as compound 4,

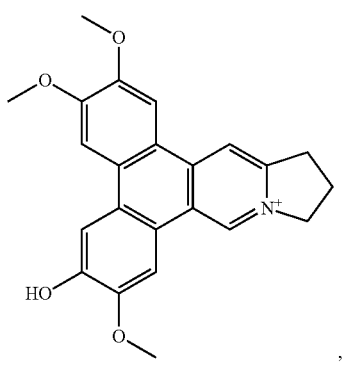

Formula (5)

a compound of Formula (6), also referenced as compound 5,

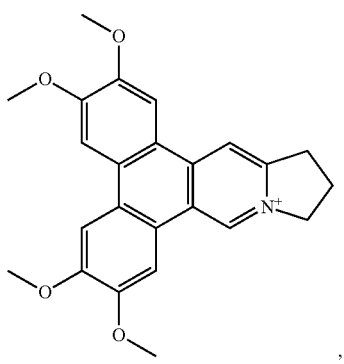

Formula (6)

a compound of Formula (7), also referenced as compound 6,

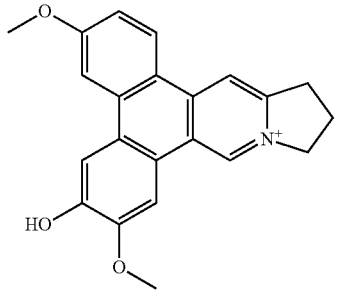

Formula (7)

and a compound of Formula (8), also referenced as compound 7,

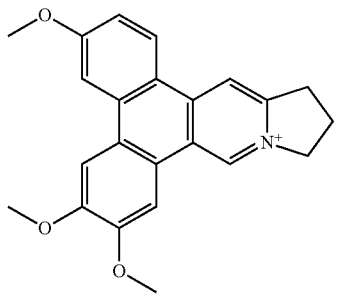

Formula (8)

In particular, the method of the present invention allows for the isolation of at least one and more preferably one phenanthroindolizidine alkaloid:
- having Formula (2);
- having Formula (3);
- having Formula (4); and/or
- having Formula (5).

The method of the present invention comprises a step (i) of subjecting *Tylophora atrofolliculata* plant material to a solvent extraction with an extraction solvent for obtaining a crude extract, wherein the extraction solvent comprises an aliphatic alcohol.

Preferably, the *Tylophora atrofolliculata* plant material comprises the whole plant, i.e. it comprises roots and aerial parts of *Tylophora atrofolliculata*. The method of the present invention may further comprise steps, before carrying out step (i), of a) drying the *Tylophora atrofolliculata* plant material, and/or b) cutting, shredding, milling and/or pulverizing the *Tylophora atrofolliculata* plant material.

For example, about 1 kg to 10 kg such as about 5.5 kg of the *Tylophora atrofolliculata* plant material can be used in the method of the present invention. The amount of *Tylophora atrofolliculata* plant material in relation to the total amount of the extraction solvent used in step (i) is preferably between 20 mg/ml and 60 mg/ml, further preferred about 42 mg/ml plant material relative to the total amount of extraction solvent used in step (i). In embodiments, the solvent extraction in step (i) is carried out three times, and the amount of *Tylophora atrofolliculata* plant material in relation to the amount of extraction solvent in each of the three solvent extractions is preferably of from 80 to 180 mg/ml, more preferably in the first solvent extraction about 100 mg/ml, in the second solvent extraction about 125 mg/ml and in the third solvent extraction about 167 mg/ml, wherein the amount of extraction solvent in the second and third solvent extraction is calculated in relation to the starting weight of the *Tylophora atrofolliculata* plant material used in the first solvent extraction.

The extraction solvent comprises an aliphatic alcohol, which means herein an aliphatic hydrocarbon, preferably a branched or straight chain alkane, wherein at least one hydrogen atom of the aliphatic hydrocarbon is substituted with a hydroxyl group, preferably one hydrogen atom is substituted with a hydroxyl group referenced as monohydric aliphatic alcohol. More preferably, the aliphatic alcohol of the extracting solvent is a monohydric aliphatic alcohol, still more preferably a monohydric alcohol with 1 to 4 carbon atoms, further preferably with 1 to 2 carbon atoms. I.e. the aliphatic alcohol of the first extracting solvent is more preferably selected from methanol, ethanol, propanol, isopropanol, n-butanol, isobutanol, sec-butyl alcohol, tert-butyl alcohol or mixtures thereof and further preferably from methanol, ethanol or mixtures thereof. More preferably, the aliphatic alcohol of the extraction solvent is methanol. The extraction solvent most preferably essentially consists of methanol.

The solvent extraction in step (i) is preferably carried out for 4 to 10 h in total. In embodiments, the solvent extraction in step (i) is carried out three times, and each of the three solvent extractions is carried out for 2 to 4 h, more preferably the first solvent extraction is carried out for about 4 h, the second solvent extraction for about 2 h and the third solvent extraction for about 2 h.

The temperatures are preferably above 45° C., in particular at least 50° C., and most preferably the *Tylophora atrofolliculata* plant material is refluxed with the extraction solvent.

The solvent extraction in step (i) is preferably carried out at least two, more preferably at least three times and in particular three times, wherein the extracts obtained in each step are combined for forming the crude extract. Thus, in especially preferred embodiments of the present invention, the *Tylophora atrofolliculata* plant material is refluxed with the extraction solvent, in particular methanol, at least two times, in particular three times. I.e. the solvent extraction of step (i) is preferably carried out three times with the *Tylophora atrofolliculata* plant material.

Preferably, the extraction solvent is removed before step (ii) for forming the crude extract, i.e. step (i) preferably further comprises removing the extraction solvent after the solvent extraction and before step (ii). The extraction solvent is preferably removed by evaporation under reduced pressure.

The method of the present invention further comprises a step (ii) of contacting the crude extract obtained in step (i) with a first and a second separation solvent for obtaining a first and a second layer, wherein the first separation solvent comprises and preferably essentially consists of water and the second separation solvent comprises an ester. The ester is in particular a $C_1$-$C_6$ aliphatic alcohol ester of a $C_1$-$C_7$ alkyl carboxylic acid. Further preferably, the ester is a $C_3$-$C_7$ ester, in particular ethyl acetate or ethyl formate. In most preferred embodiments of the present invention, the second separation solvent comprises and preferably essentially consists of ethyl acetate. In particular, the first separation solvent is mainly comprised in the first layer and the second separation solvent is mainly comprised in the second layer obtained. More specifically, the first layer in particular comprises the at least one phenanthroindolizidine alkaloid and the main part of the first separation solvent. The second layer comprises the main part of the second separation solvent. "Main part" usually means more than 90% of the total amount of the separation solvent, preferably more than 95%. The term "layers" used herein and as generally understood by the skilled person means separated phases resulting from contacting at least two solvents which are substantially immiscible or immiscible with each other, in the present invention for example the first and the second separation solvent.

Preferably, contacting the crude extract with the first and the second separation solvent in step (ii) means sequentially adding the first and the second separation solvent to the crude extract. In preferred embodiments of the present invention, the crude extract is added, preferably suspended, in the first separation solvent. Preferably, the pH of the suspension is adjusted to less than 3, in particular to about 1 to 2 before adding the second separation solvent, preferably by adding an inorganic (mineral) acid, in particular by adding HCl. Then the second separation solvent is preferably added accompanied by shaking for forming the first and the second layer and the first layer is then separated. Such procedure is especially suitable for separating chlorophyll and neutral compounds from the phenanthroindolizidine alkaloids.

Preferably, the pH of the first layer is adjusted to at least pH 8 by adding a base before step (iii), in particular by adding an alkali hydroxide. I.e. the base is preferably an alkali hydroxide. Alkali hydroxides are a class of chemical compounds which are composed of an alkali metal cation, i.e. one of lithium (Li), sodium (Na), potassium (K), rubidium (Rb), caesium (Cs), and the hydroxide anion (HO—). In particular, the alkali metal cation is K or Na. More preferably, the base is NaOH. Most preferably, the first layer is basified by adding 10% NaOH for obtaining a pH of about 9 to 10 before step (iii).

The method of the present invention further comprises a step (iii) of contacting the optionally basified first layer obtained and in step (ii) with a third separation solvent for forming a third layer, which third separation solvent comprises a halogenated hydrocarbon. The third layer in particular comprises the main part of the third separation solvent. The third layer in particular does not comprise the at least one phenanthroindolizidine alkaloid or comprises only traces of the at least one phenanthroindolizidine alkaloid.

The third separation solvent is added to the first layer preferably accompanied by shaking for forming the third layer.

The term "halogenated hydrocarbon" as used herein refers to a hydrocarbon, preferably an alkane, which hydrocarbon has at least one hydrogen atom substituted with a halogen atom. Preferably, the halogenated hydrocarbon in the first extracting solvent is a hydrocarbon, preferably a branched or straight chain alkane, which hydrocarbon has 1 to 4 carbon atoms and wherein at least one hydrogen atom is substituted with a halogen selected from Br, Cl, or F, in particular from Cl. Preferably, the halogenated hydrocarbon is an alkane with 1 to 2 carbon atoms in which at least one hydrogen atom is substituted with a Cl atom, in particular selected from methyl chloride, dichloromethane or chloroform. Most preferably, the halogenated hydrocarbon in the third separation solvent is chloroform. In further preferred embodiments of the present invention, the third separation solvent essentially consists of chloroform.

The method of the present invention further comprises a step (iv) of contacting the first layer after step (iii) which in particular comprises the first separation solvent and the at least one phenanthroindolizidine alkaloid with a fourth separation solvent comprising an aliphatic alcohol for forming a fourth layer. The fourth layer in particular comprises the main part of the fourth separation solvent and the at least one phenanthroindolizidine alkaloid. The aliphatic alcohol of the fourth separation solvent is preferably a monohydric aliphatic alcohol, more preferably a monohydric alcohol with 1 to 5 carbon atoms, further preferably with 4 carbon atoms. I.e. the aliphatic alcohol of the fourth separation solvent is more preferably selected from n-butanol, isobutanol, sec-butyl alcohol, tert-butyl alcohol or mixtures thereof and more preferably n-butanol. The fourth separation solvent most preferably essentially consists of n-butanol.

The method of the present invention further comprises a step (v) of subjecting the fourth layer to at least a first chromatographic separation step, preferably carried out with liquid column chromatography including separating by means of fragmentation.

Preferably, step (v) further comprises a step of removing the solvent portion of the fourth layer, i.e. in particular the fourth separation solvent, before carrying out the first chromatographic separation step. The solvent portion is preferably removed by means of evaporation in vacuum.

In preferred embodiments of the present invention, at least the first and a second chromatographic separation step are carried out in step (v).

At least a first and a second chromatographic separation step are carried out in step (v) for isolating a phenanthroindolizidine alkaloid:
having Formula (2)
having Formula (3);
having Formula (4);
having Formula (5);
having Formula (6);
having Formula (7); and/or
having Formula (8).

Chromatographic separation steps in step (v) are preferably carried out with liquid chromatography including column chromatography and can be carried out as classical (low pressure) column chromatography usually operating with a low pressure up to about 0.5 MPa, high-performance liquid chromatography (HPLC) usually with operational pressures up to 5 MPa or higher. HPLC can be carried out as semi-preparative or preparative HPLC.

Preferably, the first chromatographic separation step is selected from classical (low pressure) column chromatography, in particular with unmodified silica gel (further referenced as "silica gel"). The silica gel preferably has a particle size of about 40 µm to about 63 µm.

The second chromatographic separation step and any further chromatographic separation steps preferably comprise liquid chromatography, which may be carried out as classical column chromatography or HPLC. Preferably, the second and any further chromatographic separation step is carried out with HPLC. The stationary phase is preferably selected from a reverse phase, in particular a C18 reverse phase. Preferably, HPLC is used for the second and any further chromatographic separation step, wherein a C18 reverse phase is used as stationary phase having a particle size of about 5 µm, a pore size of 130 Å and preferably column dimensions of about 250×10 mm.

The first chromatographic separation step is preferably carried out by means of classical column chromatography and preferably includes fractionating the fourth layer and its components, respectively, to obtain several fractions, in particular at least 10 fractions, more preferably at least 12 fractions, i.e. including collecting individual eluate fractions rich in the at least one phenanthroindolizidine alkaloid to be isolated. The first chromatographic separation step is preferably carried out as gradient elution, i.e. with a gradient of eluting solvents.

More preferably, the first chromatographic separation step is carried out with silica gel as stationary phase and preferably with eluting solvents selected from a halogenated hydrocarbon, a $C_1$ to $C_3$ aliphatic alcohol, a $C_1$ to $C_3$ carboxylic acid or mixtures thereof, preferably at least two of chloroform, methanol, and formic acid. More preferably, all of chloroform, methanol and formic acid are applied for establishing a gradient elution.

In particular, chloroform-methanol-formic acid are used as elution solvents and more preferably the elution solvents are applied with a gradient of 10:0:0.05 to 0:10:0.05.

Preferably, by subjecting the fourth layer in particular after removing the solvent portion to silica gel and eluting with elution solvents chloroform-methanol-formic acid, at least 10 fractions more preferably at least 12 fractions are selected. The 12 fractions are further referenced as "fraction no. xx" or "Fr.".

The fractions are preferably selected based on a thin layer chromatography (TLC) monitoring which is usual practice in the art, i.e. the number and size of each fraction is determined by the specific composition and changes in the composition as well as the presence of alkaloids. I.e. a change in the composition confirmed with TLC means next fraction. For example, when a new compound shows up in the eluted part compared with the already eluted parts confirmed with TLC, this represents a new fraction until there is a change in the composition, e.g. said new compound is no longer eluted. The presence of alkaloids can be verified with usual and well-known reagents. TLC is preferably carried out with silica gel, in particular silica gel 60 $F_{254}$.

For isolating the phenanthroindolizidine alkaloids having Formula (2) and (3) given above, 12 fractions are collected as defined above, wherein fraction no. 10 is preferably subjected to a repeated HPLC.

For isolating the phenanthroindolizidine alkaloids having Formula (4) and (5) given above, 12 fractions are collected as defined above, wherein fraction no. 11 is preferably subjected to repeated HPLC.

For isolating the phenanthroindolizidine alkaloids having Formula (6) to (8) given above, 12 fractions are collected as defined above, wherein fraction no. 12 is preferably subjected to repeated HPLC.

In another aspect, the present invention refers to a phenanthroindolizidine alkaloid, namely a compound selected from the group consisting of:
a compound of Formula (2);
a compound of Formula (3);
a compound of Formula (4); and
a compound of Formula (5)
which can be isolated from *Tylophora atrofolliculata* by the method described above.

Further in accordance with the present invention is a composition, preferably a pharmaceutical composition, comprising and in particular essentially consisting of:
at least one, in particular one phenanthroindolizidine alkaloid, in particular as pharmaceutically effective ingredient, isolated from *Tylophora atrofolliculata* according to the method described above, and at least one pharmaceutically tolerable excipient such as one or more of a diluent, a filler, a binder, a disintegrant, a lubricant, a coloring agent, a surfactant and a preservative.

The phenanthroindolizidine alkaloid comprised in the composition, in particular in the pharmaceutical composition, is preferably of Formula (1) as described above.

In more preferred embodiments of the present invention, the phenanthroindolizidine alkaloid comprised in the composition is one of:
a compound of Formula (2);
a compound of Formula (3);
a compound of Formula (4);
a compound of Formula (5);
a compound of Formula (6);
a compound of Formula (7);
or a compound of Formula (8).

In further preferred embodiments of the present invention, the phenanthroindolizidine alkaloid comprised in the composition is one of:
a compound of Formula (2);
a compound of Formula (3);
a compound of Formula (4);
a compound of Formula (5);
a compound of Formula (6);
or a compound of Formula (7).

In more preferred embodiments of the present invention, the phenanthroindolizidine alkaloid comprised in the composition is one of:
a compound of Formula (2);
a compound of Formula (3);
a compound of Formula (4);
or a compound of Formula (5).

In most preferred embodiments of the present invention, the phenanthroindolizidine alkaloid comprised in the composition is one of:
a compound of Formula (2);
or a compound of Formula (5).

The phenanthroindolizidine alkaloid is contained in the composition, in particular the pharmaceutical composition, preferably in an effective amount, i.e. an amount suitable to treat or prevent a disease in a subject, in particular a human, which also depends on the frequency and number of compositions to be administered. For example, the phenanthroindolizidine alkaloid may be used in an amount equivalent to the amount of telomeric G-quadruplexes of a targeted population of cancer cells, in particular for those phenanthroindolizidine alkaloids which exhibit 1:1 binding stoichiometry with the G-quadruplexes. The skilled person is able to select a suitable effective amount of the phenanthroindolizidine alkaloid based on the conditions required.

The skilled person is also able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

The pharmaceutical composition according to the invention can be present in solid, semisolid or liquid form to be administered by an oral, rectal, topical, parenteral or transdermal or inhalative route to a subject, preferably a human.

The pharmaceutical composition may comprise further pharmaceutical effective ingredients such as therapeutic compounds used for treating cancer. The pharmaceutical composition may be provided in form of a kit comprising the pharmaceutical composition described above and at least one further pharmaceutical composition having another active ingredient for treating cancer.

Further in accordance with the present invention is a method of treating a subject suffering from cancer comprising administering an effective amount of at least one phenanthroindolizidine alkaloid, preferably one phenanthroindolizidine alkaloid, isolated from *Tylophora atrofolliculata* according to the method described above to the subject.

In particular, the method comprises administering an effective amount of at least one phenanthroindolizidine alkaloid and preferably the phenanthroindolizidine alkaloid is of Formula (1) as described above.

More preferably, the method comprises administering an effective amount of a phenanthroindolizidine alkaloid selected from the group consisting of:
a compound of Formula (2);
a compound of Formula (3);
a compound of Formula (4);
a compound of Formula (5);
a compound of Formula (6);
a compound of Formula (7);
and a compound of Formula (8)
which can be isolated from *Tylophora atrofolliculata* by the method described above.

Further preferably, the method comprises administering an effective amount of a phenanthroindolizidine alkaloid selected from the group consisting of:
a compound of Formula (2);
a compound of Formula (3);
a compound of Formula (4);
and a compound of Formula (5).

Most preferably, the method comprises administering an effective amount of a phenanthroindolizidine alkaloid selected from the group consisting of:
a compound of Formula (2);
and a compound of Formula (5).

The subject is an animal or human, preferably it is a mammal and most preferably a human. The expression "effective amount" generally denotes an amount sufficient to produce therapeutically desirable results, wherein the exact nature of the result varies depending on the specific disorder which is treated. When the disorder is cancer, the result is usually an inhibition or suppression of the proliferation of the cancer cells, a reduction of cancerous cells or the amelioration of symptoms related to the cancer cells. In particular, the effective amount used herein refers to an amount capable of exhibiting telomerase inhibitory effect by binding the targeted telomeric G-quadruplexes.

The effective amount of the phenanthroindolizidine alkaloid isolated from *Tylophora atrofolliculata* may further depend on the species, body weight, age and individual conditions of the subject and can be determined by standard procedures such as with cell cultures or experimental animals.

Another aspect relates to a method of treating a subject suffering from cancer comprising:
isolating at least one and preferably one phenanthroindolizidine alkaloid from *Tylophora atrofolliculata* by the method described above, in particular a phenanthroindolizidine alkaloid of Formula (1):

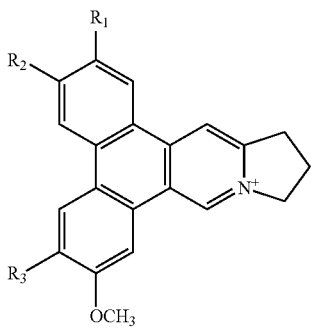

Formula (1)

wherein $R_1$, $R_2$ and $R_3$ are each independently selected from a hydrogen atom, a hydroxyl group, an alkyl group, or an alkoxy group, in particular $R_1$ is selected from H, OH or $OCH_3$ and $R_2$ and $R_3$ are each independently selected from OH or $OCH_3$;

formulating the at least one phenanthroindolizidine alkaloid into a pharmaceutically composition; and administering said pharmaceutical composition to a subject suffering from cancer. The subject is preferably a human.

Further in accordance with the present invention is at least one phenanthroindolizidine alkaloid isolated from *Tylophora atrofolliculata* with the method described above for use in the treatment of cancer and the use of the at least one phenanthroindolizidine alkaloid isolated from *Tylophora atrofolliculata* with the method described above for preparing a medicament for the treatment of cancer. The phenanthroindolizidine alkaloid in particular is at least one and preferably one of:

a compound of Formula (2);
a compound of Formula (3);
a compound of Formula (4);
or a compound of Formula (5).

More preferably, the phenanthroindolizidine alkaloid is at least one and preferably one of:

a compound of Formula (2);
or a compound of Formula (5).

EXAMPLES

Example 1

Materials Used and Conditions Applied

UV data were recorded using a Beckman DU 800 UV/vis spectrophotometer. HRESIMS were recorded on an Agilent 6230 ESI-TOF mass spectrometer. NMR spectra were obtained from Bruker Ascend™ 600 spectrometer equipped with a cyro platform. Silica gel (Devisil®, 40~63 micron) was used for column chromatography. Silica gel plates (Merck, DC Kieselgel 60 $F_{254}$) was used for TLC analysis. High-performance liquid chromatography (HPLC) was carried out on Agilent 1100, Agilent 1200 and Waters 1525-2489 apparatus with a semi-preparative column (Waters, XBridge® Prep C18, 5 μm, 250×10 mm). 27 nt human telomeric DNA (M monoisotopic=8492.4 Da, Invitrogen) was used for G-quadruplex binding assay, which was the same as the one applied in Bai, L. P. et al. PloS One 2013, 8, e53962. The G-quadruplex binding analysis was conducted on a Bruker maXis impact mass spectrometer equipped with a kdScientific syringe pump (Holliston, Mass., USA). Solvents for HPLC separation analysis were HPLC grade.

The whole plant of *T. atrofolliculata* was collected in Guangxi province, China in 2012 and identified by Dr. Zhifeng Zhang (Faculty of Chinese Medicine, Macau University of Science and Technology). A voucher specimen (No. MUST-TA201302) was deposited at State Key Laboratory of Quality Research in Chinese Medicine, Macau University of Science and Technology.

Example 1A

Isolation of Phenanthroindolizidine Alkaloids from *T. atrofolliculata*

The whole plant of *T. atrofolliculata* (5.5 kg) was refluxed with methanol for three times to afford a crude extract, namely with amounts of 55 L, 44 L and 33 L of methanol subsequently. Totally 8 h were spent for the solvent extraction, which has been carried out for three times following the order of 4 h, 2 h, and 2 h subsequently. The crude extract after methanol evaporation under reduced pressure was suspended in water as first separation solvent then adjusted to pH 1~2 by adding hydrochloric acid. After being partitioned with ethyl acetate as second separation solvent, the acidic aqueous phase as first layer was basified with 10% sodium hydroxide to pH 9~10 then extracted with chloroform as third separation solvent to afford a third layer. The third layer was discarded and the first layer further partitioned with n-butanol as a fourth separation solvent to afford a fourth layer with the crude alkaloids (75 g).

The fourth layer after evaporation of n-butanol was chromatographed over silica gel rendering 12 fractions, which were further separated through repeated column HPLC to afford 7 phenanthroindolizidine alkaloids (compounds 1 to 7).

The crude alkaloid extract (10 g) was subjected to silica gel column chromatography with chloroform-methanol-formic acid (10:0:0.05-0:10:0.05) to obtain 12 fractions based on the TLC behavior Fr. 10 was separated by repeated HPLC to obtain compound 1 (0.6 mg) and compound 2 (0.6 mg). Similarly, compound 3 (0.7 mg) and compound 4 (0.7 mg) were obtained from Fr. 11, while compound 5 (1 mg), compound 6 (7 mg) and compound 7 (7 mg) were separated from Fr. 12.

The chemical structures of compounds 1 to 6, corresponding to compounds of Formulas (2) to (7) were elucidated by means of NMR methods including $^1H$-$^1H$ COSY, NOESY, HSQC and HMBC experiments, assisted by high-resolution MS and CD spectral analysis. In order to obtain unambiguous NMR spectra, compounds 1 to 6 were all treated with hydrochloric acid to form chloric salt form before performing NMR measurement.

Compound 1, i.e. compound of Formula (2) was obtained as yellow amorphous powder. Its formula was determined as $C_{23}H_{22}NO_4$ by ion peak at m/z 376.1561 $[M]^+$ (calcd 376.1549 for $C_{23}H_{22}NO_4$). The UV spectrum displayed strong absorption bands at 287 (4.58), 330 (4.09) nm, which were similar to those of quaternary phenanthroindolizideine moiety (UV (MeOH) $\lambda_{max}$ (log ε) 253 (4.25), 287 (4.58), 330 (4.09) nm). The $^1H$ NMR spectrum (Table 1) indicated two 1, 2, 4, 5-tetra-substituted benzene rings ($\delta_H$ 8.01, 7.99, 7.65, 7.64, each s), two aromatic singlets ($\delta_H$ 10.12, 8.79, each s), four methylene triplets ($\delta_H$ 5.05, 3.69, each 2H, t, J=7.2 Hz), two methylene multiplets ($\delta_H$ 2.68, 2 H, m) and three methoxyl groups ($\delta_H$ 4.18, 4.11, 4.15, each 3H, s). The $^{13}C$ NMR spectrum (Table 2) present twenty-three carbon resonances corresponding to seventeen aromatic (eleven quaternary carbons including four oxygenated and one nitrogenated ones), three methylene (one nitrogenated methylene group), two methoxyl carbons. These data suggested that compound 1 is a quaternary alkaloid with similar moiety to that of compound 5. The difference was ascribed to an additional hydroxyl group instead of methoxyl group assigned at C-2 based on the carbon signal at $\delta_C$ 147.4 (Table 2). The methyl groups were determined to be located at C-3, C-6, C-7 on the basis of the HMBC correlations of $OCH_3$-3 with C-3, $OCH_3$-6 with C-6, $OCH_3$-7 with C-7, and the NOESY correlations $OCH_3$-3/H-4, $OCH_3$-6/H-5, $OCH_3$-7/H-8 (FIG. 1). Thus, compound 1 was elucidated as 2-demethyldehydrotylophorine (see Formula (2)).

Figure 2:
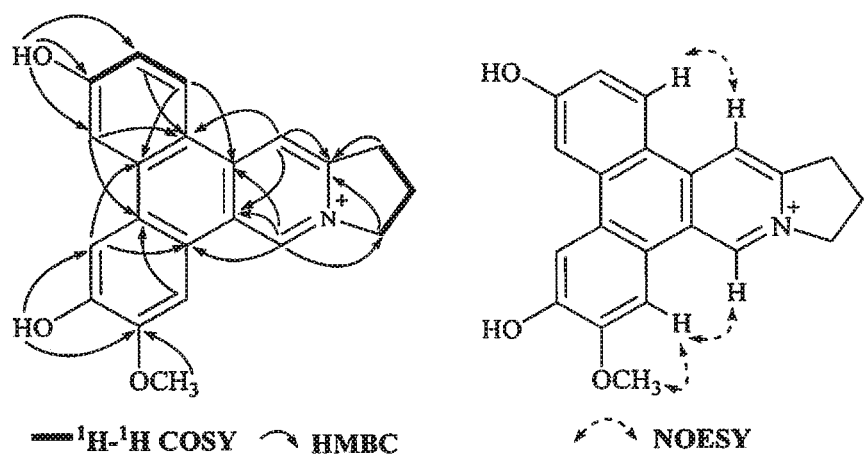
FIG. 2 shows the correlations observed in $^1$H-$^1$H COSY, HMBC, and NOESY spectra of compound of Formula (3), also referenced as compound 2.

Compound 2, i.e. compound of Formula (3) was obtained as yellow amorphous powder. Its molecular formula $C_{21}H_{18}NO_3$ was derived from ion peak at m/z 332.1288 [M]$^+$ (calcd 332.1287 for $C_{21}H_{18}NO_3$). The UV spectrum displayed strong absorption bands at 263 (4.17), 287 (4.30), 360 (3.65) nm. The $^1$H NMR spectrum of compound 2 (Table 1) suggested the presence of three aromatic protons with a ABX system [$\delta_H$ 8.79 (d, J=9.0 Hz), 7.82 (d, J=1.8 Hz), 7.27 (dd, J=1.8, 9.0 Hz)], one 1, 2, 4, 5-tetra-substituted benzene rings (8.21, 7.93 each s), two aromatic singlets ($\delta_H$ 10.39, 9.08, each s), four methylene triplets ($\delta_H$ 4.96, 3.56, each 2H, t, J=7.2 Hz), two methylene multiplets ($\delta_H$ 2.53, 2 H, m), one methoxyl group ($\delta_H$ 4.08, 3 H, s), and two hydroxyl groups ($\delta_H$ 10.90, 10.30, each s). Compound 2 possessed similar NMR data as those of tylophoridicine D (Tables 1 and 2). The differences were ascribed to the additional two hydroxyl groups rather than methoxyl groups, which were decided to be placed at C-3 and C-6 on the basis of carbon resonances at $\delta_C$ 161.0 and 150.3 (Table 2). The HMBC correlations of OH-3 with C-2, C-3 and C-4, OH-6 with C-5 and C-7 further confirmed these placements (FIG. 2). The remaining methoxyl group was linked to C-7 on the basis of HMBC correlation of $OCH_3$-7/C-7 as well as NOESY correlation $OCH_3$-7/H-8 (FIG. 2). Thus, compound 2 was characterized as 3-demethylanhydrodehydrotylophorinidine (see Formula (3)).

Figure 3:
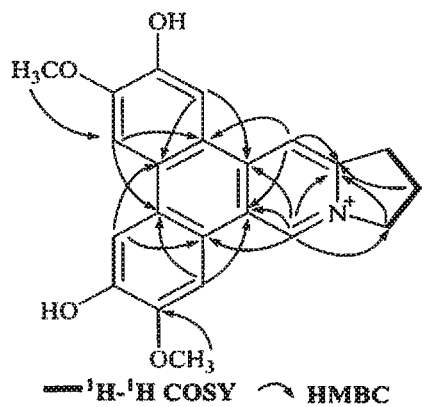
FIG. 3 shows the correlations observed in $^1$H-$^1$H COSY, HMBC, and NOESY spectra of compound of Formula (4), also referenced as compound 3.

Compound 3, i.e. compound of Formula (4) was obtained as yellow amorphous powder. The molecular formula $C_{22}H_{20}NO_4$ was determined from the ion peak at m/z 362.1397 [M]$^+$ (calcd. 362.1392 for $C_{22}H_{20}NO_4$). The UV spectrum displayed strong absorption bands at 253 (4.13), 288 (4.49), 334 (3.91) nm. The NMR data of compound 3 closely matched to those of compound 1 except for the presence of an additional hydroxyl group instead of methoxyl group placed at C-6 on the basis of the carbon resonance at $\delta_C$ 149.1 (Table 2). The remaining hydroxyl group was assigned at C-2 on the basis of its carbon resonance at $\delta_C$ 147.2 (Table 2). The methoxyl groups were determined to be located at C-3 and C-7 based on the HMBC correlations of $OCH_3$-3 with C-3, $OCH_3$-7 with C-7 (FIG. 3). Thus, compound 3 was elucidated as 2-hydroxylanhydrodehydrotylophorinidine (see Formula (4)).

Compound 4, i.e. compound of Formula (5) was obtained as yellow amorphous powder. Its formula $C_{23}H_{22}NO_4$ was determined from ion peak at m/z 376.1564 [M]$^+$ (calcd. for $C_{23}H_{22}NO_4$), suggesting that it is a isomer of compound (1). The UV spectrum displayed strong absorption bands at 253 (4.17), 286 (4.52), 330 (3.95) nm. The NMR data of compound 4 were similar to those of compound 3 (Tables 1 and 2) except for the methoxyl group rather than the hydroxyl group at C-2 on the basis of HMBC correlations of $OCH_3$-2 with C-2, and the NOESY correlation $OCH_3$-2/H-1 (FIG. 4).

Figure 4:
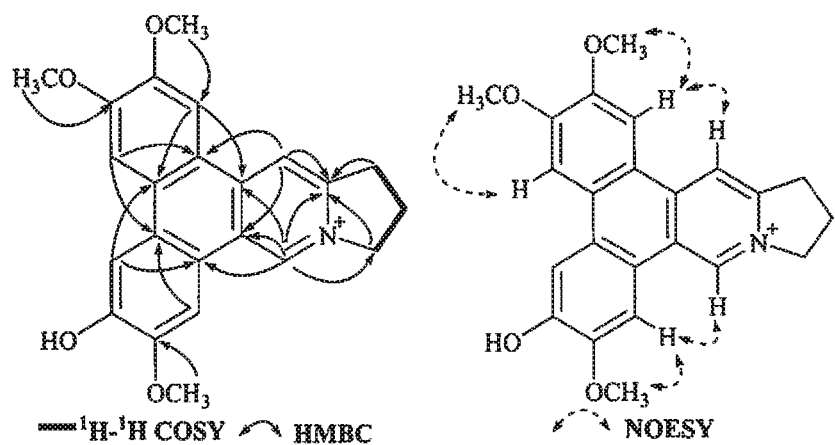
FIG. 4 shows the correlations observed in $^1$H-$^1$H COSY, HMBC, and NOESY spectra of compound of Formula (5), also referenced as compound 4.
Figure 5I:
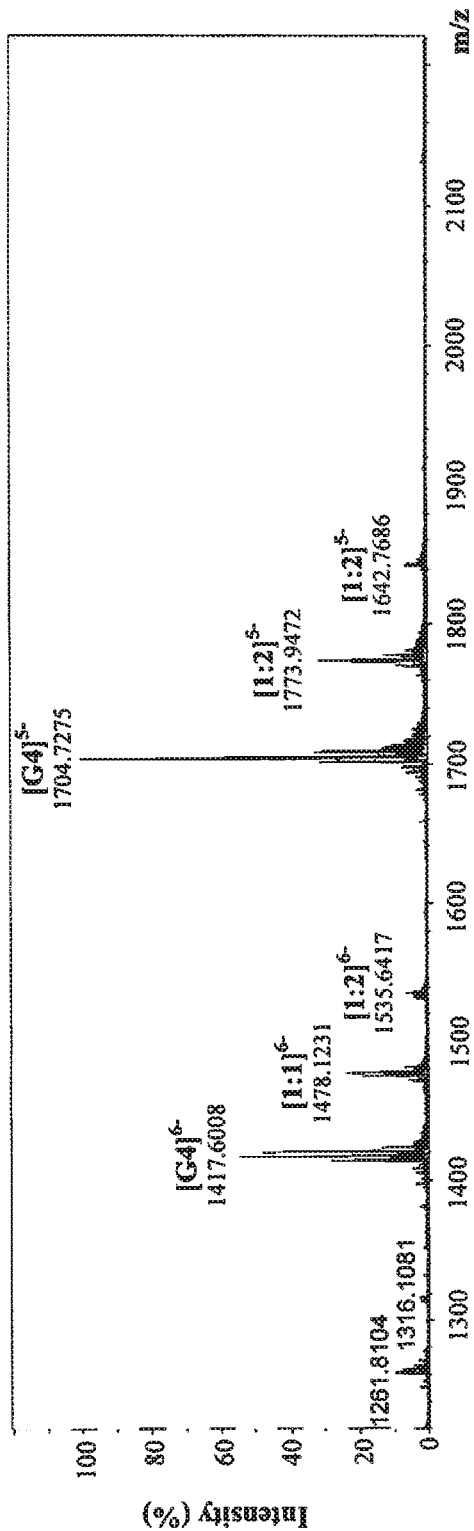
FIG. 5I shows the negative ESI-TOF-MS spectrum of human telomeric sequence (G4) in the presence of an equimolar amount of compound of Formula (8), also referenced as compound 7.
Figure 5J:
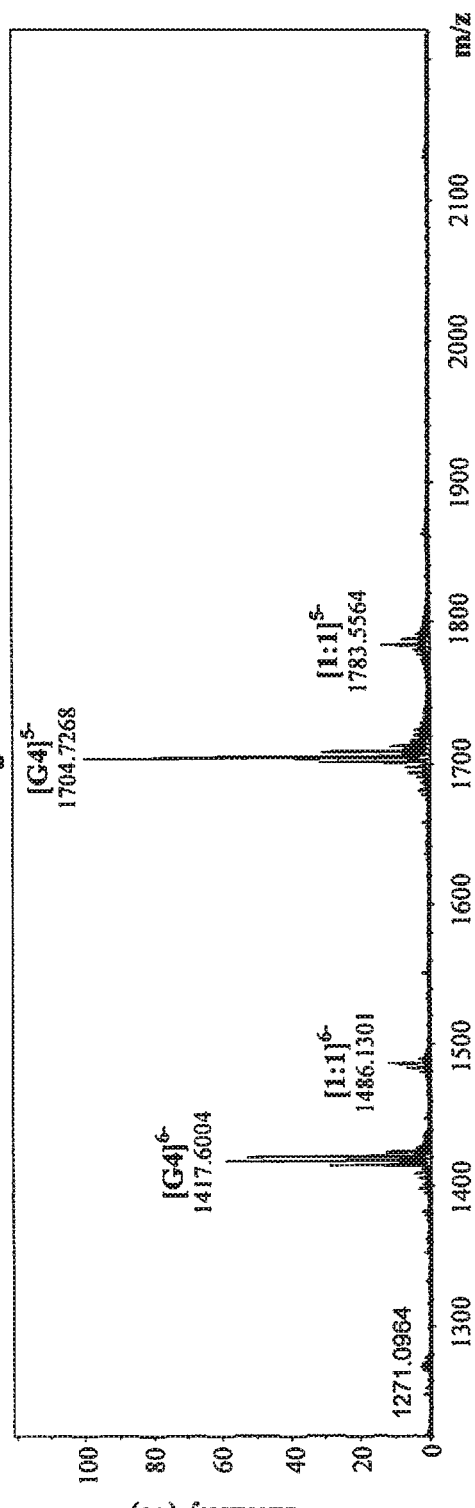
FIG. 5J shows the negative ESI-TOF-MS spectrum of human telomeric sequence (G4) in the presence of an equimolar amount of a compound of Formula (9), also referenced as compound 8.

The rest two methoxyl groups were thus placed at C-3, C-7 through the HMBC correlations of $OCH_3$-3 with C-3, $OCH_3$-7 with C-7 as well as the NOESY correlations $OCH_3$-3/H-4, $OCH_3$-7/H-8 (FIG. 4). The hydroxyl group was determined to be placed at C-6 based on the carbon resonance at $\delta_C$ 149.5 (Table 2). Therefore, compound 4 was identified as 6-demethyldehydrotylophorine (see Formula (5)).

Compound 5, i.e. compound of Formula (6) was obtained and identified as dehydrotylophorine (Govindachari, Indian J. Chem., 1973, 11, 1215; and Chuang T. H., Org. Biomol. Chem., 2006, 4, 860-867) (see Formula (6)).

Compound 6, i.e. compound of Formula (7) was obtained as yellow powder. The NMR data of 6 closely resemble those of 2 except for the methoxyl group rather than hydroxyl group placed at C-3, which was confirmed by the HMBC correlation of $OCH_3$-3 with C-3. The rest methoxyl group was placed at C-7 on the basis of the HMBC correlation of $OCH_3$-7 with C-7. The hydroxyl group was thus determined to be placed at C-6 on the basis of the carbon resonance at $\delta_C$ 148.0 (Table 2). Thus, compound 6 was elucidated as an hydrodehydrotylophorinidine, which was firstly reported by Govindachari (Govindachari, Indian J. Chem., 1973, 11, 1215), who only presumed that structure without interpreting from NMR spectral data. $^1$H and $^{13}$C NMR spectroscopic data of compound 6 were measured and present in Tables 1 and 2 (see Formula (7)).

Compound 7, i.e. compound of Formula (8) was obtained and determined as tylophoridicine D.

TABLE 1

$^1$H NMR spectroscopic data of compounds 1 to 4 and 6 ($\delta$ in ppm, J in Hz).

| position | 1$^a$ | 2$^b$ | 3$^a$ | 4$^a$ | 6$^a$ |
|---|---|---|---|---|---|
| 1 | 8.01, s | 8.79, d, 9.0 | 7.87, s | 7.93, s | 7.98, d, 6.6 |
| 2 | | 7.27, dd, 1.8, 9.0 | | | 6.86, d, 7.2 |
| 4 | 7.65, s | 7.82, d, 1.8 | 7.47, s | 7.62, s | 6.67, s |
| 5 | 7.64, s | 7.93, s | 7.57, s | 7.70, s | 6.81, s |
| 8 | 7.99, s | 8.21, s | 7.88, s | 7.94, s | 7.12, s |
| 9 | 10.12, s | 10.39, s | 9.99, m | 10.01, s | 9.38, s |
| 11 | 5.05, t, 7.2 | 4.96, t, 7.2 | 5.01, m | 4.92, t | 4.77, s |
| 12 | 2.68, m | 2.53, m | 2.67, m | 2.56, t | 2.57, s |
| 13 | 3.69, t, 7.2 | 3.56, t, 7.2 | 3.65, m | 3.57, t | 3.45, s |
| 14 | 8.79, s | 9.08, s | 8.64, s | 8.83, s | 8.18, s |
| $OCH_3$-2 | | | | 4.01, s | |
| $OCH_3$-3 | 4.18, s | | 4.11, s | 4.00, s | 3.86, s |
| $OCH_3$-6 | 4.11, s | | | | |
| $OCH_3$-7 | 4.15, s | 4.08, s | 4.16, s | 4.06, s | 3.98, s |
| OH-3 | | 10.90, s | | | |
| OH-6 | | 10.30, s | | | |

$^a$Measured in CD$_3$OD.
$^b$Measured in DMSO-d$_6$.
$^c$Overlapped signals.

TABLE 2

$^{13}$C NMR spectroscopic data of compounds 1 to 4 and 6 ($\delta$ in ppm).

| position | 1$^a$ | 2$^b$ | 3$^a$ | 4$^a$ | 6$^a$ |
|---|---|---|---|---|---|
| 1 | 109.3 | 129.0 | 109.1 | 105.8 | 126.9 |
| 2 | 147.4 | 118.0 | 147.2 | 149.8 | 115.4 |
| 3 | 152.6 | 161.0 | 152.3 | 153.7 | 161.8 |
| 4 | 104.1 | 108.0 | 103.6 | 104.0 | 104.5 |
| 5 | 103.8 | 109.0 | 107.7 | 108.0 | 107.6 |
| 6 | 149.9 | 150.3 | 149.1 | 149.5 | 148.0 |
| 7 | 151.5 | 150.0 | 148.6 | 149.1 | 148.6 |
| 8 | 104.2 | 105.9 | 103.9 | 104.1 | 103.5 |

TABLE 2-continued

13C NMR spectroscopic data of compounds 1 to 4 and 6 (δ in ppm).

| position | 1[a] | 2[b] | 3[a] | 4[a] | 6[a] |
|---|---|---|---|---|---|
| 9 | 137.5 | 138.5 | 137.1 | 137.4 | 136.3 |
| 11 | 58.2 | 58.5 | 58.1 | 58.2 | 57.9 |
| 12 | 21.8 | 22.4 | 21.7 | 21.8 | 21.3 |
| 13 | 31.0 | 31.6 | 30.9 | 31.0 | 30.8 |
| 13a | 150.1 | 151.1 | 149.6 | 149.9 | 149.5 |
| 14 | 115.9 | 116.2 | 115.8 | 116.1 | 115.2 |
| 4a | 127.5 | 135.2 | 127.3 | 128.6 | 133.3 |
| 4b | 125.2 | 124.9 | 125.4 | 125.4 | 123.5 |
| 8a | 119.2 | 119.9 | 118.3 | 119.9 | 118.6 |
| 8b | 124.3 | 124.1 | 124.5 | 124.7 | 123.1 |
| 14a | 139.2 | 139.8 | 138.9 | 139.1 | 138.7 |
| 14b | 119.3 | 117.7 | 119.1 | 119.8 | 117.4 |
| OCH3-2 |  |  |  | 55.5 |  |
| OCH3-3 | 55.6 |  | 55.2 | 55.3 | 54.8 |
| OCH3-6 | 55.4 |  |  |  |  |
| OCH3-7 | 55.3 | 56.7 | 55.6 | 55.6 | 55.9 |

[a]Measured in CD3OD.
[b]Measured in DMSO-d6.
[c-e]Overlapped signals.

Example 1B

Analysis of the G-Quadruplex Binding Activity of the Phenanthroindolizidine Alkaloids Isolated in Example 1A Electrospray ionization time-of-flight mass spectrometry (ESI-TOF-MS) experiments were conducted on a Bruker maXis impact mass spectrometer in the negative mode (Bai, L. P., Plos One, 2013, 8, e53962; Bai, L. P., Sci. Rep. 2014, 4, 6767). The ESI source parameters were set as follows: end plate offset voltage of 500 V, capillary voltage of 3000 V, nebulizer of 1.0 bar, dry gas flow of 4.0 L/min at 160° C. The flow rate of sample injection into the mass spectrometer was set at 3 uL/min by using a kdScientific syringe pump. Each mass spectrum was obtained by an average of at least 30 scans. The mixture of a final concentration of 10 uM nucleic acid, i.e. human telomeric DNA (27 nt) (M=8496.6 Da), and 10 uM phenanthroindolizidine alkaloid in 10 mM ammonium acetate was directly injected into mass spectrometer. Data were obtained from three parallel samples of nucleic acid-drug complex solution, and then analyzed with the software of Compass DataAnalysis.

ESI-TOF-MS was utilized to investigate the non-covalent binding capacity of compounds 1 to 7, i.e. compounds of Formulas (2) to (8) with human telomeric DNA G-quadruplex formed by the human telomeric sequence. The human telomeric sequence is known and disclosed in Bai, L. P. et al. PloS One 2013, 8, e53962. 13aS-tylophorine compound 8, i.e. compound of Formula (9):

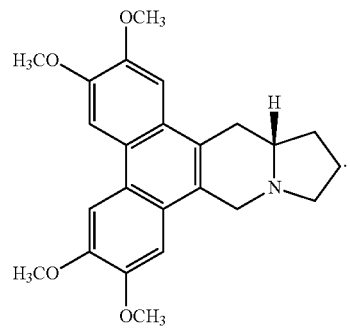

Formula (9)

and reference G-quadruplex binder sanguinarine were used as control (Bai, L. P., Anal. Bioanal. Chem., 2008, 392, 709; Bai, L. P., Bioorg. Med. Chem., 2006, 14, 5439). As presented in FIGS. 5A to 5J, compounds 1, and 3 to 7 exhibited both 1:1 and 1:2 binding stoichiometry, demonstrating that one to two molecules of them probably binds to the G-quadruplex. 1:1 binding stoichiometry was observed with compounds 2 and 8, suggesting that only one molecule of these two compounds binds to the G-quadruplex DNA. The relative binding affinities (RBA) of tested compounds were calculated to evaluate their binding capacities to human telomeric DNA G-quadruplex using the equation:

RBA=Σcomplexes peaks areas/ΣG-quadruplex DNA peaks areas

As shown in Table 3, compound 7 possessed the highest RBA value (0.619) among all tested phenanthroindolizidine alkaloids. Although compound 2 had the lowest RBA value (0.122) for its relatively weak binding strength with human telomeric DNA G-quadruplex, compound 2 is also capable of binding to the telomeric G-quadruplex DNA.

TABLE 3

Relative binding affinity (RBA) of compounds 1 to 8 and sanguinarine.

| Compound | RBA |
|---|---|
| 1 | 0.265 ± 0.008 |
| 2 | 0.122 ± 0.007 |
| 3 | 0.189 ± 0.002 |
| 4 | 0.238 ± 0.010 |
| 5 | 0.290 ± 0.017 |
| 6 | 0.437 ± 0.019 |
| 7 | 0.619 ± 0.016 |
| 8 | 0.168 ± 0.007 |
| sanguinarine | 0.735 ± 0.043 |

Values are means ± SD, where SD = standard deviation. All experiments were independently performed at least three times.

Structure and activity relationship (SAR) based on the analysis of these RBA values revealed that quaternary ammonium cation and molecular planarity favored higher G-quadruplex DNA binding capacity. Compound 5 showed a higher RBA value (0.290) than that of its hydrogenated counterpart compound 8 (0.168), while compound 8 was characterized by the absence of positive charge at nitrogen atom, and shortened conjugated system at indolizidine ring leading to decreased planarity. Secondly, substitution of methoxyl/hydroxyl group at C-2 may affect DNA binding affinity, i.e. with a lower DNA binding affinity. The RBA value of compound 7 (0.619) was at least 2 times higher than that of its 2-methoxylated/hydroxylated analogues compound 5 or 1 (0.290 or 0.265). The same tendency could be observed between RBA values of compound 6 (0.437) and that of its 2-methoxylated/hydroxylated analogues compound 4 or 3 (0.238 or 0.189). Finally, methylation of hydroxyl group strengthened binding affinity, which was exemplified by the observation at C-6, C-3, and C-2. Compounds 1, 5 and 7 (0.265, 0.290, 0.619) showed higher RBA values than those of their 6-demethyl counterparts 3, 4 and 6 (0.189, 0.238, 0.437). Compound 6 (0.437) showed at least 3 times potency in RBA value than that of its 3-demethyl analogue compound 2 (0.122), while compound 4 (0.238) possessed higher RBA value than that of its 2-demethyl analogue compound 3 (0.189).

It will be appreciated by persons skilled in the art that the embodiments described can be used in part or wholly with any of the embodiments described herein. It will also be appreciated that portions or elements that are known in the prior art or known to persons skilled in the art have not been explicitly described. It will also be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of binding a telomeric G-quadruplex DNA in a sample comprising the step of adding a phenanthroindolizidine alkaloid isolated from *Tylophora atrofolliculata* into the sample,
wherein the phenanthroindolizidine alkaloid is of Formula (1),

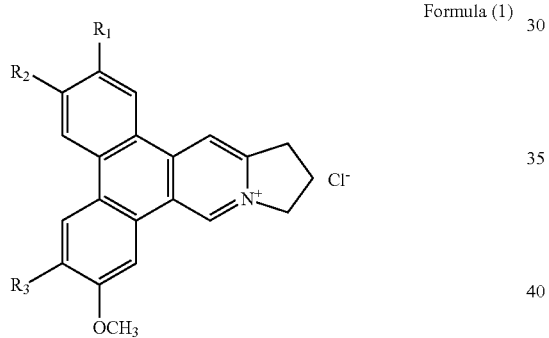

Formula (1)

wherein $R_1$ is selected from H, OH or $OCH_3$ and $R_2$ and $R_3$ are each independently selected from OH or $OCH_3$, and phenanthroindolizidine alkaloid is a planar conformation.

2. The method of claim 1, wherein the phenanthroindolizidine alkaloid is selected from the group consisting of:
a compound of Formula (2)

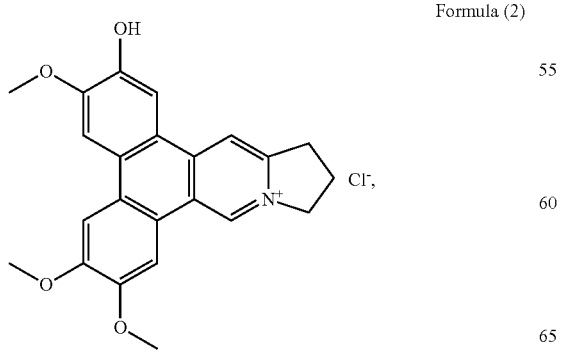

Formula (2)

a compound of Formula (3)

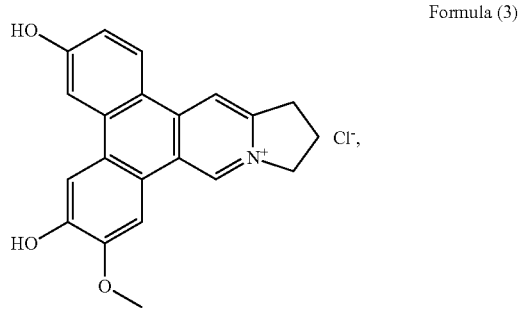 [SMILES: COc1cc2c(cc1O)c1cc(O)ccc1c1cc3[n+](cc21)CCC3]

Formula (3)

a compound of Formula (4)

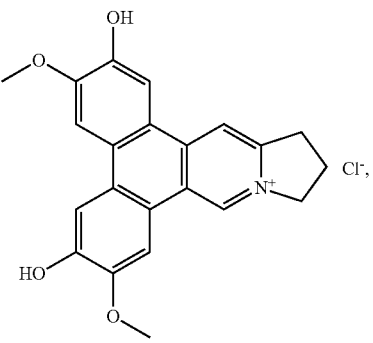

Formula (4)

a compound of Formula (5)

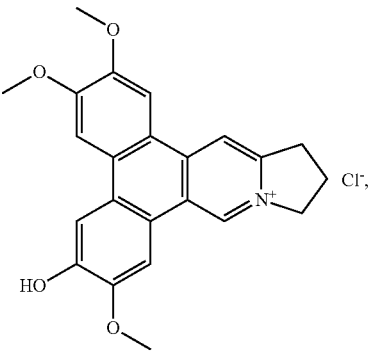

Formula (5)

a compound of Formula (6)

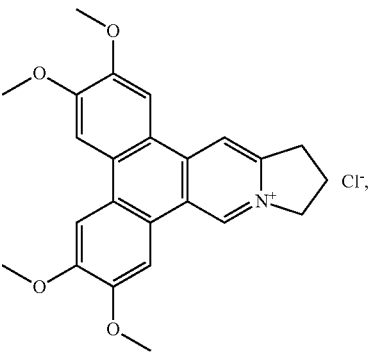

Formula (6)

a compound of Formula (7)

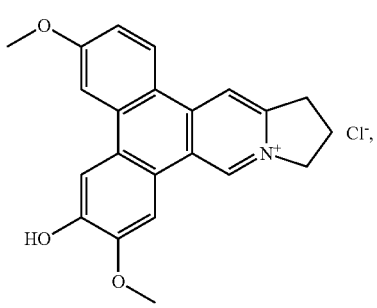

Formula (7)

and a compound of Formula (8)

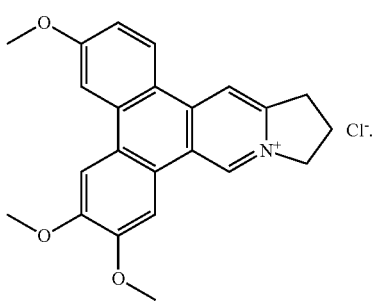

Formula (8)

3. The method of claim 1, wherein the phenanthroindolizidine alkaloid is selected from the group consisting of:
a compound of Formula (2)

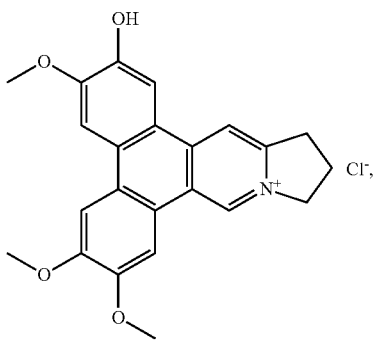

Formula (2)

a compound of Formula (3)

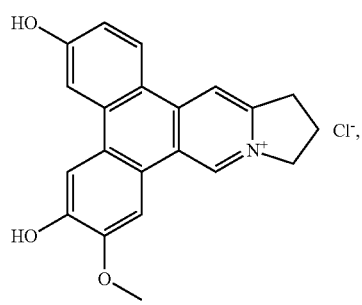

Formula (3)

a compound of Formula (4)

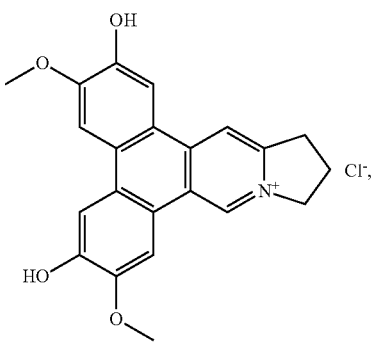

Formula (4)

and a compound of Formula (5)

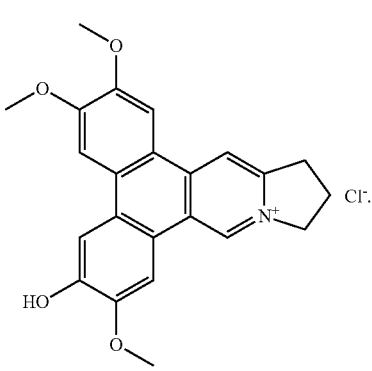

Formula (5)

4. The method of claim 1, wherein the phenanthroindolizidine alkaloid is selected from the group consisting of:
a compound of Formula (2)

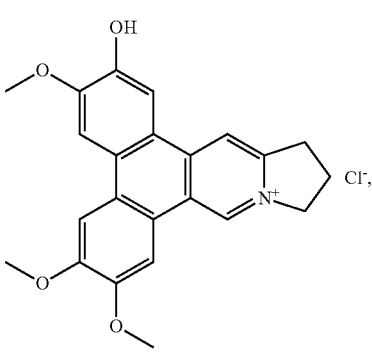

Formula (2)

and a compound of Formula (5)

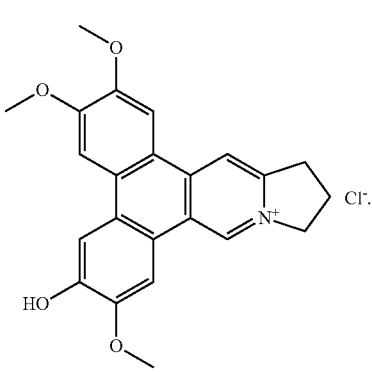

Formula (5)

5. The method of claim 1, wherein the telomeric G-quadruplex DNA is formed by a human telomeric sequence.

6. The method of claim 1, wherein the sample further includes a salt solution.

7. The method of claim 6, wherein the salt solution is a solution of ammonium acetate solution.

* * * * *